United States Patent [19]

Pierce et al.

[11] 4,357,363

[45] Nov. 2, 1982

[54] ELEMENT, STRUCTURE AND METHOD FOR THE ANALYSIS OR TRANSPORT OF LIQUIDS

[75] Inventors: Zona R. Pierce; David S. Frank, both of Rochester, N.Y.

[73] Assignee: Eastman Kodak Company, Rochester, N.Y.

[21] Appl. No.: 323,623

[22] Filed: Nov. 20, 1981

Related U.S. Application Data

[62] Division of Ser. No. 193,508, Oct. 2, 1980, which is a division of Ser. No. 973,669, Dec. 27, 1978, Pat. No. 4,258,001.

[51] Int. Cl.$^3$ ............................................. G01N 31/22
[52] U.S. Cl. .......................................... 427/2; 428/98
[58] Field of Search .................... 427/2, 145; 428/198, 428/327, 339, 442; 422/55–59; 23/230 B

[56] References Cited

U.S. PATENT DOCUMENTS 3,992,158  11/1976  Millkan ................................. 422/57

FOREIGN PATENT DOCUMENTS 2322167  3/1977  France .

*Primary Examiner*—Sam Silverberg
*Attorney, Agent, or Firm*—James L. Lewis

[57] ABSTRACT

An element for the analysis or transport of liquid, especially aqueous liquids, contains a structure comprising a plurality of heat-stable, organo-polymeric particles non-swellable in and impermeable to the liquid, and an adhesive concentrated at particle surface areas contiguous to adjacent particles bonding the particles into a coherent, three-dimensional lattice that is non-swellable in the liquid. A substantial portion of the particle surface area in this lattice structure is therefore effectively free from adhesive. The lattice structure has interconnected void spaces among the particles representing a total void volume of about 25 to 80 percent to provide for transport of the liquid. The adhesive comprises an organic polymer different from that of the particles and insoluble in the liquid under analysis. The amount of adhesive in the structure is less than 10 weight percent of the particles.

The particulate structure of these elements can contain interactive compositions useful for the analysis of various substances in liquids, especially high molecular weight proteinaceous substances in aqueous biological liquids. Multi-zone elements containing, in fluid contact, at least two zones having a particulate structure as described above or one such zone together with other functional zones are also disclosed.

6 Claims, 14 Drawing Figures

ELEMENT, STRUCTURE AND METHOD FOR THE ANALYSIS OR TRANSPORT OF LIQUIDS

This is a division of application Ser. No. 193,508, filed October 2, 1980 which is a division of application Ser. No. 973,669 now U.S. Pat. No. 4,258,001.

FIELD OF THE INVENTION

The present invention relates to elements having a particulate structure effective for the transport or analysis of liquids. These structures are particularly useful in the "dry chemistry" analysis of aqueous liquids. "Dry chemistry" analysis refers to analytical methods and techniques that are carried out using chemical reagents contained in various "dry-to-the-touch" test elements such as "dip-and-read" test strips, multilayer test elements and the like.

BACKGROUND OF THE INVENTION

An increasingly large number of analytical tests, procedures, and analyses (i.e., assays) must be performed each day on many kinds of liquid samples, including, but not limited to, aqueous biological fluids such as blood, serum, urine, cerebrospinal fluid, and the like, To effectively handle and meet critical laboratory needs, "dry chemistry" analytical elements used in these analyses should function rapidly, require minimal operator involvement, provide accurate and reproducible results, and reduce the severe fluid handling problems presented by the very nature of liquid samples.

Prior to the present invention, certain improved "dry chemistry" multilayer analytical elements were developed as described in U.S. Pat. No. 3,992,158 issued Nov. 16, 1976 to overcome many of the foregoing problems.

Nevertheless, large complex molecules and cellular structures contained in many aqueous liquid samples or used as reagents (hereinafter termed interactive compositions) in many liquid analysis procedures create particular difficulty in the design and development of "dry chemistry" analytical elements. These substances tend to clog and impede fluid flow in conventional liquid transport structures contained in many analytical elements.

The present invention provides a novel particulate structure for the transport or analysis of liquids which readily accommodates and transports many large, complex molecules and cells which may be contained in such liquids.

RELATED ART

The "dry chemistry" elements of U.S. Pat. No. 3,992,158 provide a highly effective multilayer element for analysis of liquids, especially aqueous biological liquids. These elements have an isotropically porous, non-fibrous spreading layer and a reagent layer. The spreading layer acts as an aqueous liquid transport layer.

The spreading layers of U.S. Pat. No. 3,992,158 can be prepared from a variety of materials including a "blushed" polymer material or a particular material. In the case of a particulate material, spreading layer porosity is created by interconnected open (i.e., void) spaces among the particles. Pigments, diatomaceous earth particles, microcrystalline colloid materials, and spherical particles of uniform size, such as resinous or glass beads, represent useful particulate materials for such spreading layers. Two specific types of particulate structures disclosed in the patent are structures composed of self-adhesive particulate materials and structures containing particulate materials and a separate binder as an adhesive.

In the case of particulate materials which can be rendered self-adhesive, such as heat-softenable polymer particles, one can form a porous structure as follows: A plurality of the particles are heat- or solvent-softened and compacted to form a layer of agglomerated particles in which adjacent particles are fused together at points of interparticle contact. U.S. Pat. No. 2,297,248 issued Sept. 29, 1942 and U.S. Pat. No. 2,745,141 issued May 15, 1956 disclose specific particulate structures prepared in this manner. U.S. Pat. No. 2,297,248 discloses porous filter elements prepared by compacting a plurality of acrylic polymer particles under heat or solvent action and pressure so that adjacent particles of the filter element are fused to one another at points of interparticle contact. U.S. Pat. No. 2,745,141 discloses a particulate structure made by spraying thermoplastic particles, e.g., polyethylene or polystyrene particles, through a heat zone onto a constant speed moving base. The exterior surface only of the particles becomes molten and fuses adjacent particles together and to the base.

U.S. Pat. No. 3,574,150 issued Apr. 6, 1971, represents another variant of a particulate structure composed of self-adhesive particles. This patent describes an open pore polyurethane structure composed of coherent spherical polyurethane particles of less than 10 microns in diameter. The structure is formed in situ on a suitable support by precipitating the spherical polyurethane particles from a dilute mixture of polyurethane-forming reactants dispersed in an organic diluent that serves as a non-solvent for the particulate polyurethane reaction product.

A second specific type of particulate structure described in U.S. Pat. No. 3,992,158 is that composed of particles bonded together by a separate adhesive. For example, this patent describes a porous structure composed of non-adherent particles, such as glass beads, coated with a thin adherent layer of a hydrophilic colloid, e.g., gelatin or poly(vinyl alcohol). When the colloid coating dries, the resultant porous layer structure formed by the adjacent particles retains its integrity and maintains sufficient open spaces among component particles to permit passage of aqueous liquids. U.S. Pat. No. 2,297,248 discloses that filter elements, also, can be prepared by adhering together adjacent particles of a particulate structure with a "suitable cement." However, the patent provides no examples of such filter elements and no description or examples of "suitable cements."

The general class of non-fibrous spreading layer structures described in U.S. Pat. No. 3,992,158 can effectively transport aqueous liquids as well as a variety of substances contained in such liquids. Nevertheless, improvements in the specific particulate layer structures of the types discussed above would be highly desirable to provide structures which are capable of transporting large, complex molecules, for example, macromolecules of biological origin, and cells, for example, red blood cells, that are contained in body fluids.

In structures composed of self-adherent particles as described in U.S. Pat. No. 3,992,158 and the other patents noted above, the heat- or solvent-softened particles tend to readily agglomerate and fill in the interparticle open spaces of the structure. Thus, high molecular weight substances employed in many aqueous liquid assays readily clog and impede fluid flow in such structures.

Similarly, many structures composed of particles bonded together with a separate cement or binder in the manner broadly disclosed in U.S. Pat. Nos. 3,992,158 and 2,297,248 tend to become clogged and impede fluid flow of liquids containing complex, high molecular weight substances. For example, in the course of work relating to the present invention, many structures composed of particles and a separate adhesive were found to exhibit the problem of having open spaces clogged and filled in. One apparent cause of this problem is that a substantial layer of adhesive distributed over most or all of the particle surface area in the structure can lead to "open space fill-in" by the adhesive. In addition, because of their solubility, many common adhesives, e.g., water-soluble colloids and other water-soluble polymers such as poly(vinyl-pyrolidone), exhibit reduced adhesive strength in the presence of aqueous liquids. Also, many particulate materials, e.g., cellulosic particles, tend to swell in the presence of aqueous liquids. Accordingly, when a particulate structure prepared from these materials is used to analyze aqueous liquids, structure coherency is reduced or lost, and partial or complete "open space fill-in" occurs.

SUMMARY OF THE INVENTION

The present invention provides an element having an improved particulate structure for the analysis or transport of liquid. This structure can readily accommodate many high molecular weight substances, including red blood cells, dissolved or dispersed in liquid samples or interactive compositions used in liquid analysis procedures without clogging or otherwise substantially impeding fluid transport in the element. Accordingly, the elements of the invention represent highly effective transport structures for liquids containing complex, high molecular weight substances of analytical interest. In particular, these elements represent highly effective structures for use in aqueous liquid analyses which require fluid migration of complex, high molecular weight substances within the element during the analysis procedure.

The elements of the invention can perform a highly efficient "spreading" function for liquids containing either low or high molecular weight substances of analytical interest, hereinafter termed analytes, especially high molecular weight analytes. That is, these elements have a particulate structure which can readily take up, uniformly distribute within itself, meter, and rapidly transport applied liquid samples containing any of a wide variety of analytes.

In these respects, the elements of the invention perform the same highly useful "spreading" function provided by conventional non-fibrous, particulate spreading layers employed in the multilayer elements for analysis of liquids described in U.S. Pat. No. 3,992,158. However, the transport of complex, high molecular weight substances, for example, proteinaceous substances having a molecular weight higher than albumin (which has a M.W. of about 60,000), has typically been carried out in conventional, non-fibrous, particulate spreading layer structures only with difficulty, typically exhibiting soem chromatographing problems (sometimes referred to as "ringing") or requiring extended "spread" times (i.e., the time required for the structure to take up, distributed within itself, and transport an applied liquid sample) on the order of a minute or more.

The elements of the invention have a particulate structure comprising a plurality of heat-stable, organo-polymeric particles non-swellable in and impermeable to the liquid under analysis and an adhesive for these particles comprising an organic polymer different from that of the particles. The adhesive is concentrated on the surface of the heat-stable particles in areas contiguous to adjacent particles and bonds the particles into a coherent, three-dimensional lattice that is non-swellable in the liquid under analysis. This lattice contains interconnected void spaces among the particles representing a total void volume of about 25 to 80 percent to provide transport of the aqueous liquid and preferably to render the lattice isotropically porous. The organo-polymeric particles typically have a particle size of from about 1.0 to 200 microns. The adhesive for these particles is insoluble in the liquid under analysis and is present in the element in an amount less than about 10 percent by weight, preferably less than 5 percent by weight, based on the weight of the heat-stable particles.

Because the adhesive contained in the element is concentrated at particle surface areas contiguous to adjacent particles, the three-dimensional lattice structure of the element exhibits a high void volume which remains substantially free from adhesive. Moreover, because the element contains a small amount of adhesive based on the weight of organo-polymeric particles, there is little or no excess adhesive available to clog and fill in the interconnected void spaces of the three-dimensional lattice. The non-swellability and impermeability properties of the organo-polymeric particles and the insolubility property of the adhesive represent further important factors contributing to the retention of high void volume and advangtageous liquid analysis and transport properties provided by the element of the invention.

In an especially preferred embodiment of the invention, analytical elements are provided for the analysis of an analyte contained in an aqueous liquid sample. These elements comprise an ineractive composition for detection of the analyte in the aqueous sample associated with a particulate structure, as described above, in which the organo polymeric particles are impermeable and non-swellable to water and the adhesive is water insoluble. In these elements, the interactive composition for analyte detection is associated with the particulate structure in a manner effective to provide fluid contact between the interactive composition and the particulate structure. The interactive composition can therefore be present in the matrix of the particulate structure; it can be located in a separate zone of the element in fluid contact with the particulate structure; or certain components of the interactive composition for analyte detection can be located in the particulate structure and other components of the interactive composition can be distributed in one or more separate zones of the element which are in fluid contact with the particulate structure. In the letter two cases, an analytical element is provided which represents a multi-zone element having at least one zone comprising the aforementioned particulate structure in fluid contact with at least one other zone comprising a separate reagent zone containing one or more components of an interactive composition for analyte detection.

In a further embodiment, interactive compositions useful for the detection of various analytes present in liquids are affixed to the surface of the organo-polymeric particles contained in the particulate structure of these elements. In a further aspect of this embodiment, the organic polymer of the particles advantageously contains a repeating unit comprising a chemical group representing an active bonding site for chemical attachment of an interactive composition.

In another embodiment of the invention, multi-zone elements containing, in fluid contact, at least two zones having a particulate structure, as described above, are provided. In one preferred aspect of this embodiment, the structure of each such zone has a different void size whereby large molecules are retained in one zone while smaller molecules migrate into a zone having a smaller void size.

In another especially preferred embodiment, the invention provides an analytical element having one or more zones comprising the particulate structure described above as a layer carried on a support. A radiation-transmissive support is particularly preferred to enhance and facilitate determination of detectable changes occurring in these elements by use of various radiometric detection methods. In further embodiments, analytical elements are provided which may contain one or more zones comprising a particulate structure as described above and one or more separate functional zones permeable to the liquid under analysis, such as reagent zones, registration zones, radiation-blocking zones, selectively permeable barrier zones, detectable species migration inhibiting zones, conventional isotropically porous, non-fibrous spreading zones, and the like as described in U.S. Pat. Nos. 3,992,158; 4,042,335; 4,066,403; and Smith-Lewis and Figueras U.S. Ser. No. 916,173 filed June 16, 1978. The individual zones of these multi-zone elements are preferably present as superposed layers in fluid contact with one another.

The aforementioned particulate structure and an element containing the same, as described in further detail hereinafter, can also provide effective analytical elements for immunoassays. Such immunoassay elements represent a particularly useful embodiment of the invention. Immunoassays are typically employed for analysis of extremely low concentrations of analyte contained in a liquid sample. However, the interactive compositions used in the assays, for example, immunoreagents, such as antibodies, antigens, and haptens, and various detectable species, sometimes referred to as labels, associated with these immunoreagents, often represent large, complex molecular species. Thus, "dry chemistry" analytical elements for immunoassays must be able to transport these large, complex substances without impeding, blocking, or otherwise interfering with the migration of these molecules through the element structure. The particulate structure described herein is ideal for transport of such large molecules.

The elements of the invention can be used essentially for transport of a liquid. Preferably, however, these elements can also provide for the analysis of an analyte contained in a liquid. Analysis of a liquid by the method of the invention comprises the steps of (a) contacting together the liquid and the element of the invention to interact the analyte, or a reaction product of the analyte, for example, physically or chemically, with the element to produce a detectable change within the element; and (b) detecting this change, such as by an appropriate radiometric technique, to determine the presence and/or concentration of the desired analyte.

A further embodiment of the invention provides a preferred method of making the above-described elements. This method comprises the steps of (a) forming in a liquid carrier a "stable dispersion" of the organo-polymeric particles and the organic polymeric adhesive, and (b) applying this dispersion to a support and removing the liquid carrier at a temperature below the heat-stability temperature of the organo-polymeric particles, such as by suitable drying conditions, to form, in situ, the desired particulate structure of the invention.

DESCRIPTION OF PREFERRED EMBODIMENTS

PARTICULATE STRUCTURE

Figure 1:
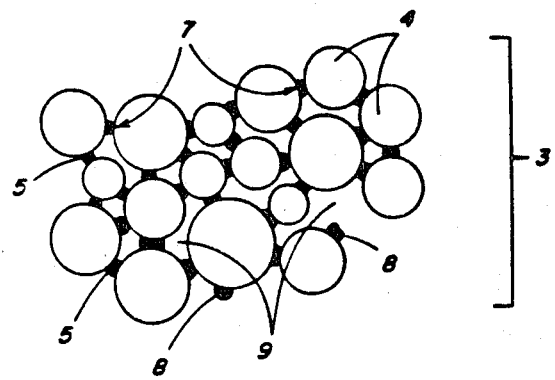
FIG. 1 is a drawing illustrating, diagrammatically, the particulate structure comprising the organo-polymeric particles and adhesive contained in the elements of the invention.

An essential feature of the invention is the coherent, three-dimensional lattice formed by the organo-polymeric particles and the adhesive for these particles. The interconnected void spaces existing among the adjacent particles of this lattice structure are essential to provide for transport of liquids and for substances, e.g., high molecular weight analytes, which may be contained in a liquid or introduced into the liquid as it is transported through the structure. Maintaining particulate integrity of the organo-polymeric particles in the lattice structure prevents the coalescence and flow of these materials into these void spaces; and the concentration of adhesive at those particle surface areas of the lattice which are contiguous to adjacent particles insures that the adhesive does not flow into and clog these spaces.

A large portion of the particle surface area present in the lattice structure is effectively free from adhesive. By retaining substantial portions of the particulate surface area effectively free from adhesive, not only is "open space fill-in" within the lattice avoided, but also these surface areas are available for use as binding sites or equivalent "fixing" sites, for any of a variety of interactive compositions useful in a particular analysis.

The concentration of the adhesive at particle surface areas contiguous to adjacent particles also prevents the adhesive from interfering with interactive compositions which may be fixed to these particle binding sites. Thus, if desired, various interactive compositions can be "pre-attached" to the surface of the organo-polymeric particles without fear that large portions of the interactive composition will be effectively overcoated, covered up, or otherwise inactivated by the adhesive contained in the particulate structure.

The void spaces in the lattice structure represent a void volume within the range of from about 25 to 80 percent. Typically, where it is desired to maximize void volume, preferred elements contain particulate structures having void volumes within the range of from about 40 to 80 percent. The presence of these interconnected void spaces provide effective fluid flowpaths through the particulate lattice structure and, preferably, renders the lattice isotropically porous.

The term "isotropically porous" and similar terms refer to porosity in all directions within the particulate structure. The degree of porosity can vary, of course, depending on void size, void volume or other parameters.

Although the size of these void spaces is comparatively large on a molecular scale and therefore capable of handling large complex molecular substances without clogging, the absolute size of these void spaces is still small. Typically, the effective mean void size exhibited by these particulate structures is within the range of from about 0.1 to 1× the mean particle size of the organo-polymeric particles contained in the structure. Thus, liquid transport is facilitated by the capillary action of the liquid being drawn through these interconnected spaces within the particulate structure of the element. Stated in other words, the interconnected void spaces in these structures represent interconnected microvoids for liquid transport.

The size of the void spaces and the void volume of the particulate structure can vary widely and will depend upon a number of factors including the size of the particles contained in the structure, the method of preparing the structure, and the like. Further detail concerning these various parameters is presented hereinafter. For any given element, the desired size of these void spaces will depend upon the particular liquid to be transported, i.e., its viscosity, and upon the size and molecular configuration of various components contained in the liquid or introduced into the liquid as interactive compositions. The size of void spaces in the particulate structures can be measured by conventional techniques such as mercury intrusion techniques. Void volume can be calculated with reasonable accuracy by a variety of techniques such as described in Chalkley, *Journal of the National Cancer Institute*, 4, p. 47 (1943) and by direct weighing and determining the ratio of actual weight of the structure to the weight of solid material equal in volume to that of the structure, comparably composed of constituents from the structure.

A further advantageous feature of the particulate structure is its "metering" capability. That is, like the conventional particulate spreading compositions described in U.S. Pat. No. 3,992,158, these particulate structures, when in a planar form, also can receive on one surface thereof, an applied liquid sample and distribute the sample within itself such that, at any given time, a uniform concentration of the liquid sample and analyte contained therein is provided at the opposite surface of the planar structure. It is possible to obtain such uniform concentrations over a range of sample volumes applied to the structure so that extremely precise sample application techniques are not required although approximate uniformity of applied sample volumes, e.g. ±10–20%, may be desirable to achieve preferred spread times or the like.

The thickness, i.e., dry thickness, of the particulate structure can vary widely depending upon the size of the organo-polymeric particles in the structure and the specific use for which the structure is intended. For example, an element having a support bearing the particulate structure as a superposed layer typically employs a particulate structure having a dry thickness within the range of from about 10 to about 500 microns. However, in certain applications, structures having a thickness outside the aforementioned range may also be employed.

Figure 2:
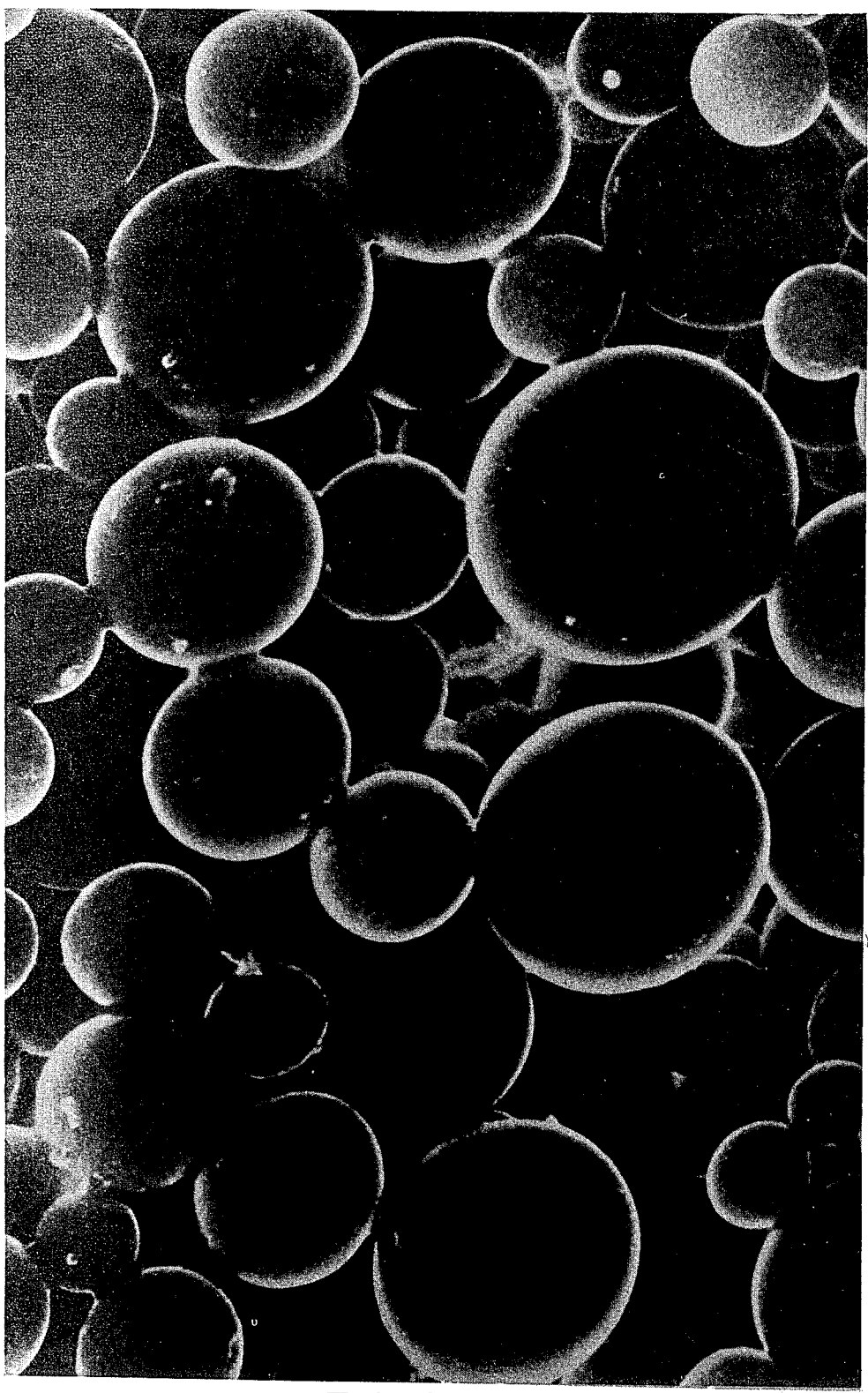
FIG. 2 is a black-and-white electron micrograph obtained under 6000× magnification showing the three-dimensional lattice formed by the heat-stable particles and the adhesive in a preferred particulate structure of the invention. The electron micrograph shows the extensive void volume provided by the interconnected void spaces of the lattice, as well as the concentration of the adhesive at those particle surface areas contiguous to adjacent particles.

To provide further illustration of the particulate structure of the invention, FIGS. 1 and 2 are attached. FIG. 1 illustrates, diagrammatically, a preferred particulate structure 3 as viewed under magnification containing an array of organo-polymeric particles 4 having an average particle size of from about 1 to 20 microns. The total amount of adhesive 5 contained in structure 3 of FIG. 1 is on the order of about 2 percent by weight based on the total weight of adhesive 5 and particles 4 contained in structure 3. In FIG. 1 adhesive 5 is concentrated on particle surface areas 7 contiguous to adjacent particles within structure 3, thereby forming the characteristic three-dimensional lattice structure of the invention. Other particle surface areas may contain some amount of adhesive as indicated by particle surface areas 8 in FIG. 1, but the adhesive is concentrated in particle surface areas 7 contiguous to adjacent particles. Therefore, large surface area portions of the majority of particles 4 contained in particulate structure 3 are effectively free from adhesive 5. Structure 3 contains a large number of interconnected void spaces 9 to provide liquid transport and to render the structure isotropically porous.

FIG. 2 is a black-and-white electron micrograph showing an actual particulate structure 3 of the invention. The electron micrograph of FIG. 2 was taken at 6000x magnification. Adhesive 5 is visible in FIG. 2 concentrated at particle surface areas 7 contiguous to adjacent particles. Interconnected void spaces 9 are also readily visible in FIG. 2.

HEAT-STABLE PARTICLES

The organo-polymeric particles employed in the present invention are heat-stable particles. "Heat-stable particles" refers to particles which, upon exposure to typical environmental temperature conditions, do not burst, become tacky, coalesce into an agglomerate of individual particles, or otherwise undergo significant physical alteration. If such physical alteration were to occur under these conditions, the void spaces in the particulate structure of the element could be effectively plugged or seriously damaged, thereby impairing the liquid transport capability of the element. The "heat stability temperature" of an organo-polymeric particle refers to the maximum temperature at which the particle can retain its heat stability properties. Therefore, the heat-stability temperature of an organo-polymeric particle typically corresponds to or is higher than the glass transition temperature of the polymer component of the particle. In general, particles are considered to possess sufficient heat stability if they retain their initial physical shape and remain nontacky at temperatures extending at least over the range of from about 15° C. to 40° C., preferably from about 10° C. to 80° C.

The particles used in the invention are also impermeable and non-swellable in the particular liquid intended for transport and/or analysis by the element. These properties of the particles insure the structural integrity and retention of the void spaces within the element upon application of the liquid. As noted in the *Related Art* section, if the particles swell in the presence of liquid the void spaces of the element can become pluged. "Non-swellability" or "resistance to swell" refers to particles which exhibit little (i.e., less than about 20%, preferably less than 10% swell) or no swelling as determined by a swellability test. With respect to aqueous liquids, such a test can be carried out by forming a self-supporting film of the specific polymer under consideration for use as a particle material or a layer of the polymer, such layer having a dry thickness of from about 50 to 200 microns, on a suitable support, for example, a polystyrene film support, and evaluating the swell properties of this film or layer in the presence of the desired liquid by use of a swellometer of the type described in A. Green and G. I. P. Levenson, *Journal of Photographic Science*, 20, 205 (1972). Using this swellometer, the swell properties of the film or layer can be measured by determining the percent increase in the film or layer thickness which results from immersing the dry film or layer into a liquid bath at 38° C. for 2.5 minutes.

Although shape and size of the organo-polymeric particles can vary widely, in a preferred embodiment these particles are of substantially uniform size. Typically, the particles have a curvilinear surface and most preferably the particles are substantially spherical beads. Generally, these particles have a particle size within the range of from about 1.0 to about 200 microns.

The size of the organo-polymeric particles regulates, to an extent, the size of the void spaces contained in the particulate structure of the element. In a preferred embodiment, wherein the particulate structure of the element is intended for the transport of aqueous liquids containing complete cellular structures such as red blood cells which can attain a size range of from about 6 to 8 microns, one would select large size particles for use in the elements of the invention. In such case, particle sizes within the range of from about 20 to 200 microns, preferably about 20 to 100 microns can be employed.

In the case where one is concerned with the transport of large, complex molecules, such as macromolecules of biological origin, for example, lipoproteins, antigens, and the like, somewhat smaller, although still relatively large particles having a size range on the order of from about 2 to 20 microns, preferably about 2 to 10 microns can be employed. In the case of aqueous fluids containing analytes of still smaller molecular size, for example, glucose molecules and the like, one can employ particles having a size within the range of from about 1.0 to 5 microns.

As noted, an especially preferred embodiment is an element having a particulate structure capable of transporting aqueous liquids containing large complex molecular substances; and accordingly, elements containing particulate structures employing particle sizes within the range of from about 2 to 200 microns represent an especially preferred and advantageous embodiment of the invention.

Based on the organo-polymeric composition and the properties of impermeability and non-swellability exhibited by the particles employed in the invention, these particles are also insoluble in the liquid under analysis. Insolubility of a specific material refers herein to insolubility of the material in the particular liquid of interest, e.g., water, as measured at 20° C. and, in the case of water, at a pH of about 7.0. The particles employed in the invention are typically and preferably solid (i.e., not hollow) particles. This is not an essential requirement, however, providing the particles have adequate heat-stability as discussed above.

The organo-polymeric composition of the particles can be composed of a wide variety of organic polymers, including both natural and synthetic polymers having the requisite impermeability and non-swellability properties. Because the elements can be employed to analyze a variety of liquids which can have widely varying properties, the particlar organo-polymeric composition of these particles should be selected to match the particular liquid for which a specific element is intended. Thus, the organo-polymeric particles selected need not be impermeable and non-swellable in all liquids, but only that liquid for which an element containing such organo-polymeric particles is intended for use. Such organo polymers can be thermosetting, thermoset or thermoplastic polymers. The polymers can be addition polymers or condensation polymers, such as polyesters, polycarbonates, polyamides, silicone polymers, etc. Preferably, the organo-polymeric particles are composed of addition polymers, including addition homopolymers and addition copolymers prepared from 2 or more addition polymerizable monomers. Especially preferred in accord with one embodiment of the invention are addition copolymers prepared from a blend of two or more different addition polymerizable monomers.

Both the organo polymers of the heat-stable particles and the adhesive polymers described hereinafter in the Adhesive Section can be prepared by any of a variety of conventional polymerization methods. Typical addition polymerization methods include: solution polymerization (followed by an appropriate precipitation procedure in the case of polymers formed into heat-stable particles), suspension polymerization (sometimes called bead polymerization), emulsion polymerization, dispersion polymerization, and precipitation polymerization. Condensation polymers used in the preparation of the heat-stable particles and the polymeric adhesive can be prepared by conventional condensation polymerization processes, e.g., bulk and hot-melt polymerization.

In an especially preferred embodiment, the particular organo polymer selected contains one or more reaction sites to link various interactive compositions to the surface of the particles. This embodiment is particularly useful wherein the element of the invention contains an interactive composition within the particulate structure for use in an analytical reaction scheme used to detect the analyte of interest. Of course, where the element of the invention is employed solely as an aqueous transport structure, or where a particular interactive composition contained in the structure is fixed within the structure by physical means such as adsorption to the particle surface, or where it is unnecessary to fix the interactive composition within the particulate structure, organo polymers without the above-described reaction sites can readily be employed in these particles.

In accord with an especially preferred embodiment wherein the organo polymeric particles selected must be water impermeable and water-nonswellable, a partial listing of representative addition homopolymers and copolymers useful for the organo-polymeric particles include polymers prepared from an addition polymerizable blend of monomers. Particularly, useful addition polymerizable blends of monomers are blends wherein the total monomer composition of the blends have the following composition:

a. from 0 to 100, preferably 0 to about 99, weight percent of a polymerizable, amino-substituent-free styrene monomer including derivatives and equivalents thereof, for example, a styrene monomer having the following formula

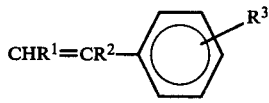

wherein each of $R^1$ and $R^2$, which may be the same or different, represents a non-interfering substituent such as hydrogen, halo, or a substituted or unsubstituted, amino-free alkyl or aryl group having 1 to about 10 carbon atoms and $R^3$ represents a non-interfering substituent such as hydrogen, halo, or a substituted or unsubstituted, amino-free aliphatic or aromatic group having 1 to about 10 carbon atoms, e.g., alkyl, alkoxy, aryl, or aryloxy group. Typical of such styrene monomers are styrene, vinyltoluene, t-butylstyrene, and equivalents thereof.

b. from 0 to about 25 weight percent of a polymerizable acrylic ester including derivatives and equivalents thereof, such as an acrylic ester having the formula

wherein $R^1$ is as defined above and $R^4$ represents a hydrocarbyl group having from 1 to about 10 carbon atoms including hydrocarbyl groups such as aryl groups, alkyl groups, alkaryl groups, aralkyl groups, e.g., benzyl groups, and the like.

c. from 0 to 100, preferably 0 to about 75, weight percent of a polymerizable methacrylic ester including derivatives and equivalents thereof, such as a methacrylic ester having the formula

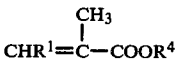

wherein $R^1$ and $R^4$ are as defined above.

d. from 0 to about 30 weight percent of a carboxylic acid containing one or more polymerizable ethylenically unsaturated groups, such as methacrylic acid, acrylic acid, crotonic acid, itaconic acid, and equivalents thereof;

e. from 0 to about 75 weight percent of a nitrile containing one or more polymerizable ethylenically unsaturated groups, such as acrylonitrile, methacrylonitrile, and equivalents;

f. from 0 to about 20 weight percent of a polymerizable amine-substituted styrene monomer, including styrene monomers having N-alkyl substituted amino substituents on the phenyl ring of the styrene monomer, such amine-substituted styrene monomers typically having the formula

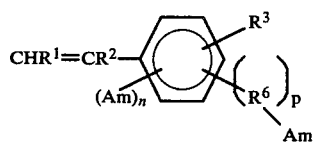

wherein each of n and p, which can be the same or different, represent 0 or 1, $R^1$-$R^3$ are as defined above, $R^6$ represents an alkylene group having from 1 to about 6 carbon atoms, and Am represents a primary, secondary, or tertiary amino group. Typical of such amine-substituted styrene monomers are N,N-dimethyl-N-vinylbenzylamine and styrenes containing N-alkyl substituted amino substituents, such as N-methylaminoethylstyrene and N,N-dimethylaminoethylstyrene.

g. from 0 to about 20 weight percent, preferably 0 to about 10 weight percent, of an addition polymerizable monomer containing a crosslinkable group, including (1) addition polymerizable monomers which can be crosslinked by conventional gelatin hardeners, for example, aldehyde hardeners, haloethylsulfonyl hardeners, bis(vinylsulfonyl) hardeners, and the like. Particularly preferred such monomers which can be crosslinked by conventional gelatin hardeners are addition polymerizable monomers containing an active methylene group as described in U.S. Pat. Nos. 3,459,790; 3,488,708; 3,554,987; 3,658,878; 3,929,482; and 3,939,130; and (2) addition polymerizable monomers which can be crosslinked by diamines, such monomers containing a conventional gelatin hardening group, for example, aldehyde group-containing monomers, haloethylsulfonyl group-containing monomers, vinylsulfonyl group-containing monomers, and the like;

h. from 0 to about 20 weight percent of a polymerizable tertiary aminoalkyl acrylate or methacrylate monomer and equivalents thereof, such as dimethylaminoethyl acrylate, diethylaminoethyl methacrylate, and the like;

i. from 0 to 100, preferably 0 to about 75, weight percent of a polymerizable, N-heterocyclic vinyl monomer and equivalents thereof, such as 4-vinylpyridine, 2-vinylpyridine, and the like;

j. from 0 to about 20 weight percent of a polymerizable acrylamide or methacrylamide monomer and equivalents thereof, including monomers having the formula

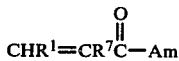

wherein $R^1$ and Am are as defined above and $R^7$ represents hydrogen or methyl. Typical of such acrylamide or methacrylamide monomers are N-isopropylacrylamide or N,N-dialkylacrylamide or N,N-dialkylmethacrylamide; and k. from 0 to about 20 weight percent, preferably 0 to about 5 weight percent, of a crosslinking monomer containing at least two addition polymerizable groups, such as divinylbenzene, N,N-methylenebis(acrylamide), ethylene diacrylate, ethylene dimethacrylate, and equivalents thereof.

It is understood, of course, that the above-noted monomer blend compositions that contain 100 weight percent of a single monomer result in addition homopolymers.

A partial listing of representative polymers for use in making the organo-polymeric particles is set forth in Table I. The numbers in brackets following each of the polymer names represents the weight ratio of monomers contained in the monomer blend from which the polymers are polymerized.

TABLE I

1. Polystyrene
2. Poly(styrene-co-methacrylic acid) [98/2]
3. Poly(vinyltoluene-co-p-t-butylstyrene-co-methacrylic acid) [61/37/2]
4. Poly(vinyltoluene-co-p-t-butylstyrene-co-methacrylic acid-co-divinylbenzene) [60/37/2/1]
5. Poly(methyl methacrylate)
6. Poly(styrene-co-vinylbenzyl chloride-co-methacrylic acid) [78/20/2]
7. Poly(styrene-co-N,N,N—trimethyl-N—vinylbenzyl-ammonium chloride-co-methacrylic acid) [88/10/2]
8. Poly(styrene-co-divinylbenzene) [98/2]
9. Poly(styrene-co-butyl acrylate-co-methacrylic acid) [88/10/2]
10. Poly(styrene-co-methacrylic acid-co-divinylbenzene) [70/25/5 and 98/1/1]
11. Poly(vinylbenzyl chloride-co-methacrylic acid-co-divinylbenzene) [93/2/5]
12. Poly(styrene-co-2-hydroxyethyl methacrylate-co-methacrylic acid) [88/10/2]
13. Poly(methyl methacrylate-co-butyl acrylate) [70/30]
14. Poly(styrene-co-acrylonitrile) [70/30]
15. Poly(methyl methacrylate-co-N—(m- and p-vinylbenzyl)-N,N—dimethylamine hydrochloride-co-ethylene dimethacrylate) [70/20/10]
16. Poly(methyl methacrylate-co-2-(N,N—diethylamino)-ethyl methacrylate hydrochloride-co-ethylene dimethacrylate) [70/20/10]

The particles typically comprise at least about 25 weight percent and preferably 50 weight percent or more of the above-described organo-polymeric composition. In many embodiments, these particles are composed entirely, i.e., 100 weight percent, of such organo-polymeric material. The remainder of these particles can be composed of other addenda, for example, colorants such as pigments or dyes; radiation-blocking agents including colorants and other opacifying addenda; fluors; fillers, magnetic addenda, e.g., magnetite; and the like, provided the requisite impermeability and non-swellability properties of the particles are maintained, and the addenda do not interfere with the analysis to be carried out in the element in which the addenda is incorporated. Broadly, such addenda can be described as noninterfering addenda and can be employed to enhance or facilitate a particular analytical procedure or test result.

ADHESIVE

The adhesive employed in the invention bonds the organo-polymeric particles to one another to provide the coherent, three-dimensional lattice of the elements. The adhesive is composed of an organo polymer different from the specific polymer contained in the particles, although quite commonly the adhesive represents a polymer containing many repeating units which are identical or similar to some of those present in the polymer composition of the particles. Within the context of the present specification, organo polymers useful for the heat-stable particles are considered different from those useful as adhesives provided they have differing viscosities and possess appropriate heat-stability or glass transition temperatures, even though they may be composed of identical repeating units.

In accord with an especially preferred embodiment, both the adhesive and the organo-polymeric particles represent an addition polymer with the adhesive representing an addition copolymer of two or more different addition polymerizable monomers, at least one of the addition polymerizable monomers of the adhesive being common to one of the monomers of the organo-polymeric particles.

The adhesive represents a polymer which, when incorporated in the particulate structure of the element, is insoluble in the liquid to be analyzed or transported by the element. Thus, suitable adhesives include polymers that are initially soluble in the liquid but become insoluble during formation of the particulate structure, for example, by crosslinking. Preferably the adhesive is also non-swellable in the liquid. However, because of the small amount of the adhesive contained in the particulate structure of these elements, namely less than 10 weight percent, preferably from about 1 to less than 5 weight percent, based on the weight of the particles contained in the structure, non-swellability of the adhesive, although preferred, is not essential.

The small amount of adhesive in the particulate structure is an important factor contributing to the desired retention of void spaces within the structure which are substantially free from and unclogged by adhesive. In accord with certain preferred embodiments, the amount of adhesive contained in the particulate structure represents from about 2 to 4.0 percent by weight based on the dry weight of th particles in the structure.

Preferred water-insoluble adhesives for use in the invention are addition homopolymers and copolymers, particularly addition copolymers, prepared from an addition polymerizable blend of monomers selected from the following group:

A. a monomer blend containing from about 1 to 35 weight percent, preferably about 10 to 30 weight percent of one or more polymerizable styrene monomers as defined in (a) above with the remainder of the blend comprising addition polymerizable monomers selected from the group consisting of alkyl acrylates or methacrylates and mixtures thereof wherein the alkyl group of these acrylates and methacrylates preferably has from 1 up to about 6 carbon atoms, such as n-butyl acrylate, n-butyl methacrylate, ethyl acrylate, and the like;

B. a monomer blend containing from about 20 to 95 weight percent, preferably 50 to 95 weight percent of monomers selected from groups (a), (b), (c), (g1), (g2), and (k), preferably groups (a)–(c) and (k) noted above such as styrene, ethyl acrylate, n-butyl acrylate, n-butyl methacrylate, 2-ethylhexyl acrylate, and methyl acrylate, with the remainder of the monomer blend comprising one or more addition polymerizable monomers having an active hydrogen or salts thereof. The term active hydrogen is defined in accord with the definition set forth by J. March, "Advanced Organic Chemistry: Reactions, Mechanisms, and Structure," McGraw, Hill, Inc., page 471 (1968) which defines active hydrogen as one which will react with methyl magnesium bromide, i.e., as in the Zerewittenoff Process. A partial listing of representative addition polymerizable monomers containing active hydrogen or salts thereof includes acrylic acid; methacrylic acid; vinylbenzyl alcohol; hydroxyalkyl acrylates and methacrylates having from 1 to about 6 carbon atoms in the alkyl group thereof; and an addition polymerizable, sulfo- or sulfate-substituted monomer, including sulfoalkyl acrylates or methacrylates such as N-sulfoalkylacrylamides or N-sulfoalkylmethacrylamides, such as 2-methyl-2-acrylamidopropane sulfonic acid, as well as the alkali metal and ammonium salts thereof, and other addition polymerizable alkyl sulfonate monomers, aryl sulfonate monomers, e.g., 4-sulfostyrene, alkyl sulfate monomers, aryl sulfate monomers, and equivalents thereof (a partial listing of representative specific addition polymerizable, sulfo- or sulfate-substituted monomers may be found in the following U.S. Pat. Nos. 2,923,734; 3,024,221; 3,265,654; 3,277,056; 3,411,911; 3,506,707; 3,525,768; and 3,547,899); addition polymerizable monomers as described in groups (g1) and (g2) above; acrylates and methacrylates of poly(alkylenediols) such as poly(ethylene glycol), for example, an acrylic ester of Tergitol ® 15-s-12, a poly(ethylene glycol) ether of a linear secondary alcohol sold by Union Carbide Corp. and alkali metal and ammonium salts of the foregoing monomers capable of such salt formation. Preferred active-hydrogen containing monomers or salts thereof include acrylic acid, methacrylic acid, 2-acrylamido-2-methylpropanesulfonic acid, and the alkali metal and ammonium salts of these acids; and C. a monomer blend containing from about 15 to 100 weight percent of one or more monomers selected from the group consisting of 1-vinylimidazole, vinylbenzyl alcohol, ethyl acrylate, or an acrylamide or a methacrylamide such as N-isopropylacrylamide with the remaining monomers of the blend comprising addition polymerizable monomers as described in group (g1) monomers above such as 2-acetoacetoxyethyl methacrylate.

It is understood, of course, that the above-noted monomer blends in group (C) that contain 100 weight percent of a single monomer result in addition homopolymers.

Table II sets forth a partial listing of representative polymers of sufficient water-insolubility to be useful as water-insoluble adhesives in the structure of the present invention. The numbers in brackets following each of the polymer names represents the weight ratio of monomers contained in the monomer blend from which the polymers are polymerized.

TABLE II

1. Poly(n-butyl acrylate-co-styrene-co-2-acrylamido-2-methylpropanesulfonic acid) [70/20/10]
2. Poly(butyl acrylate-co-styrene-co-2-acrylamido-2-methylpropanesulfonic acid) [76/21/3]
3. Poly(ethyl acrylate-co-acrylic acid-co-2-acetoacetoxyethyl methacrylate-co-2-acrylamido-2-methylpropanesulfonic acid) in the following weight ratios: (a) [71/24/4/1] and (b) [76/16/16/1]
4. Poly(vinylbenzyl alcohol)
5. Poly(ethyl acrylate)
6. Poly(N—isopropylacrylamide)
7. Poly(2-hydroxyethyl methacrylate-co-2-acetoacetoxyethyl methacrylate) [15/85]
8. Poly(n-butyl acrylate-co-acrylic acid) [75/25]
9. Poly(n-butyl acrylate-co-acrylic acid-co-methacrylic acid-co-ethyl acryloylacetate) [70/5/15/10]
10. Poly(n-butyl acrylate-co-acrylic acid-co-ethyl acryloylacetate) [75/15/10]

TABLE II-continued

11. Poly(n-butyl acrylate-co-methacrylic acid-co-2-acetoacetoxyethyl methacrylate) [56/34/10]
12. Poly(n-butyl acrylate-co-styrene) [70/30]
13. Poly(n-butyl acrylate-co-2-acrylamido-2-methylpropanesulfonic acid-co-2-acetoacetoxyethyl methacrylate) [85/10/5]
14. Poly(n-butyl acrylate-co-acrylic acid-co-2-acetoacetoxyethyl methacrylate-co-2-acrylamido-2-methylpropane sulfonic acid) [67/16/16/1]
15. Poly(n-butyl methacrylate-co-styrene) [90/10]
16. Poly(ethyl acrylate-co-styrene) [70/30]
17. Poly(n-butyl acrylate-co-2-acrylamido-2-methylpropanesulfonic acid) [90/10]
18. Poly(n-butyl acrylate-co-styrene) [50/50]
19. Poly(2-ethylhexyl acrylate-co-acrylic acid-co-2-acetoacetoxyethyl methacrylate-co-2-acrylamido-2-methylpropanesulfonic acid) [67/16/16/1]
20. Poly(n-butyl acrylate-co-methacrylic acid) [70/30]
21. Poly(ethyl acrylate-co-acrylic acid): (a) [80/20] and (b) [70/30]
22. Poly(butyl acrylate-co-styrene-co-2-acetoacetoxyethyl methacrylate-co-2-acrylamido-2-methylpropanesulfonic acid) [70/22/6/2]
23. Poly(butyl acrylate-co-styrene-co-2-acrylamido-2-methylpropanesulfonic acid-co-divinylbenzene) [69/20/10/1]
24. Poly(acrylamide-co-2-acetoacetoxyethyl methacrylate): (a) [20/80] and (b) [15/85]

Typically, the adhesive polymers have a glass transition temperature, $T_g$, which is at least 20° C., preferably 30° C., less than the heat-stability temperature of the organo polymers contained in the heat-stable particles. Preferred polymeric adhesives have a glass transition temperature below about 80° C., typically less than 30° C. (as measured under high relative humidity conditions $\geq 80\%$ RH). Adhesives having such a glass transition temperature can easily be rendered flowable without affecting the heat stability of the organo-polymeric particles with which they are combined. The term glass transition temperature is defined herein to be that temperature at which the polymer changes from a glassy polymer to a rubbery or flowable polymer. Glass transition temperatures of polymers described herein can be measured, for example, as described in "Techniques and Methods of Polymer Evaluation", Vol. 1, Marcel Dekker, Inc., N.Y. (1966).

PREPARATION OF PARTICULATE STRUCTURE

Various methods may be employed for preparing these particulate structures. In accord with a preferred embodiment, an especially useful method of making these structures comprises:

(a) forming in a liquid carrier a "stable dispersion" of the organo-polymeric particles and the organic polymer adhesive, and (b) applying this dispersion to a support and removing the liquid carrier at a temperature below the heat-stability temperature of the organo-polymeric particles, such as by suitable drying conditions. The organo-polymeric particles ar dispersed in the aforementioned "stable dispersion" to retain their particulate integrity. The organic polymer adhesive can be dispersed or dissolved in the liquid carrier vehicle of the stable dispersions. When the organic polymer adhesive is dispersed in the stable dispersion, the liquid carrier is preferably removed from the dispersion (following its application to the support) at a temperature above the glass transition temperature of the polymeric adhesive but below the heat-stability temperature of the organo-polymeric particles.

The term "stable dispersion" is defined to mean that the particles and the adhesive remain admixed in the carrier without forming an agglomerated mass of particles and adhesive. Dispersions useful in preparing the particulate structure need not remain stable for extended periods of time, but should remain as a stable dispersion for a time sufficient to apply the dispersion to a substrate serving as a temporary or permanent support for the resultant particulate structure. If the particles or adhesive settle out of the dispersion, the adhesive or particles may be redispersed by agitating the dispersion.

To accomplish the formation of such stable dispersions, a wide variety of techniques can be used. A partial listing of representative techniques is described briefly herein. These techniques can be used individually or in combination. Of course, this listing of useful techniques is not exhaustive, and therefore other techniques for formation of a stable dispersion can also be employed in step (a) of the preferred method of making these particulate structures without departing from the spirit or scope of the invention. One useful technique is the addition of a surfactant to the liquid carrier to facilitate distribution and stabilization of the particles or the adhesive in the dispersion and prevent rapid agglomeration and settling out of these components. A partial listing of representative surfactants which can be employed includes non-ionic surfactants such as Zonyl® FSN, a fluorochemical from duPont; Triton® X-100, an octylphenoxy polyethoxyethanol from Rohm and Haas; and Surfactant 10G®, a nonylphenoxypolyglycidol from Olin Corp.

In addition to the use of surfactants, formation of stable dispersions of the organo-polymeric particles and adhesives can be facilitated by controlling the order of addition of the adhesive and the particles to the liquid carrier. For example, stable dispersions of certain organo-polymer particles and adhesives, which are normally difficult to form, can be formed by first combining the particles and the liquid carrier followed by addition of the adhesive; in other cases, depending upon the particular organo-polymeric particles and adhesive, stable dispersions may be achieved by first combining the adhesive and the liquid carrier followed by addition of the particles.

Controlling the rate of addition of the organo-polymeric particles or the adhesive to the liquid carrier can also facilitate obtaining stable dispersions. For example, certain particles and adhesives, which normally do not form stable dispersions, can be formed into stable dispersions by adding only a portion of the total amount of particles to be included in the dispersion together with the adhesive, followed thereafter by the addition of the remaining amount of the particles. Similarly, this technique can be used to control the rate of addition of the adhesive by adding the adhesive in incremental amounts to a liquid carrier which already contains the total amount of the particles.

Still other techniques which can be employed to produce stable dispersions include procedures such as sonication treatments, physical blending and agitation treatments, pH adjustments, and the like.

In an especially preferred embodiment, formation of a stble dispersion is facilitated by matching the specific gravity of the organo-polymeric particles and that of the carrier liquid. When the specific gravity of the particles is matched to that of a particular carrier liquid, such particles are often referred to as "neutral buoyancy" particles. By use of neutral buoyancy particles, one can reduce or eliminate the problem whereby certain otherwise useful particles are so dense that they immediately settle out of the dispersion, rather than being distributed throughout the liquid carrier.

Neutral buoyancy particles can be prepared by regulating the polymerization process for the organo polymer of a particlar particle composition to obtain an organo polymer having a predetermined specific gravity relative to a desired carrier liquid. Alternatively, various fillers can be blended with a particlar organo polymer selected for use to obtain a resultant particle composition of polymer and filler having a bulk specific density similar to that of the desired carrier liquid.

In addition, one can match the specific gravity of the carrier liquid to that of the organo-polymeric particles by selecting a carrier liquid for use which has a specific gravity similar to that of the particles. In general, good results have been obtained in the method of the invention by selecting carrier liquid compositions and particle compositions having a specific gravity within the range of from about 0.7 to 1.3.

When the particles have a specific gravity above about 1.0, it may be desirable to introduce a viscosity modifying agent into the carrier to obtain a stable dispersion. This can be done, for example, by addition of polymeric viscosity modifying agents such as hydroxyethyl cellulose, carboxyethyl cellulose, or derivatives thereof.

In another especially preferred embodiment, the stable dispersion of the particles and the adhesive is formed using an adhesive prepared a a latex. In one such embodiment, the adhesive is separately prepared as an aqueous latex, the latex comprising the adhesive polymer and any desirable or necessary surfactants as a finely-divided discontinuous phase in an aqueous liquid vehicle as a continuous phase, and then the organo-polymeric particles are admixed with the latex. In such case, the continuous phase of the latex, e.g., the aqueous vehicle, serves as at least a portion of the liquid carrier of the stable dispersion of adhesive and organo-polymeric particles. This embodiment advantageously facilitates the maintenance of the adhesive in finely-divided, discrete form within the dispersion of adhesive and particles. This is desirable because it reduces undesired coalescence and agglomeration of the adhesive and the particles in the dispersion. In addition, it is believed that use of the adhesive in latex form promotes the concentration of the adhesive at discrete surface areas of the particles, as the liquid carrier is removed from the particles and adhesive following application of the stable dispersion to a substrate. Moreover, use of the adhesive in latex form allows one to employ water-insoluble adhesives in a dispersion containing an aqueous carrier.

When the adhesive is prepared as a latex, these latexes typically contain an amount of the polymer within the range of from about 5 to 50 weight percent, based on the total weight of the latex including the adhesive polymer, the aqueous latex vehicle, and any necessary or desirable surfactants. Such latexes can be prepared by a variety of well-known latex technique, such as those described, for example, in C. E. Schildknecht, "Vinyl and Related Polymers", John Wiley & Sons, Inc., N.Y. (1952) and C. S. Marvel, "An Introduction to the Organic Chemistry of High Polymers", John Wiley & Sons, Inc., N.Y. (1959).

In general, stable dispersions of the organo-polymeric particles and adhesive in a liquid carrier vehicle contain from about 1 to 50 weight percent of the particles and from about 0.01 to 5 weight percent of the adhesive.

Typically, the temperature of the liquid carrier during formation of the stable dispersion is at a level effective to maintain the organo-polymeric particles in a non-tacky state. That is, the temperature is maintained at a level below the heat stability temperature of these particles. This facilitates retaining the particulate integrity of the particulate structure which is, of course, highly desirable so that the void spaces of this structure remain open and unclogged.

Having formed a stable dispersion in accord with step (a) of the preferred method, step (b) is carried out by applying the dispersion to a substrate and removing the carrier liquid. Typically, this is accomplished by heating at a temperature below the heat-stability temperature of the organo-polymeric particles. In the case where the adhesive is dispersed in the stable dispersion, the liquid carrier is preferably removed at a temperature which is above the glass transition temperature of the adhesive polymer but below the heat-stability temperature of the organo-polymeric particles. The polymeric adhesive thereby enters a flowable and tacky state. In this state, adhesion to the surface of the organo-polymeric particles is facilitated. In addition, by placing the adhesive in a flowable state, one theoretically can take advantage of the capillary pressures developing between adjacent heat-stable particles as the structure is formed in situ during step (b) of the process. That is, it is believed that capillary pressure forces, which will become greatest in those regions of the structure wherein one particle is closely adjacent to the surface of another particle, can advantageously be used to draw the flowable adhesive to these regions and thereby enhance the concentration of the adhesive at those particle surface areas which are contiguous to adjacent particles.

Thus, in step (b) of the method, the stable dispersion is applied to a substrate, e.g., a temporary or permanent support, and the liquid carrier of the dispersion is removed, such as by appropriate drying conditions, to form, in situ, the desired three-dimensional particulate structure. Typical drying conditions for removal of the liquid carrier are temperatures within a range of from about 10° C. to 65° C. As step (b) is carried out, the adhesive is concentrated at surface areas of the organo-polymeric particles contiguous to adjacent particles and the adhesive bonds adjacent particles together into a coherent, particulate structure. Care should be exercised throughout step (b) of the method to avoid exceeding the heat-stability temperature of the organo-polymeric particles so that the resultant structure maintains its particulate integrity and retains the void spaces which are formed among individual particles as the liquid carrier vehicle is removed.

The size of the void spaces obtained by the method are influenced by a number of factors, including, among others, size of the organo-polymeric particles, amount of adhesive and particles contained in the stable suspension per unit volume, and rate of liquid carrier removal.

Depending upon the nature of the adhesive i.e., whether it forms a suitable bond quickly or slowly or whether it requires further curing to achieve optimum bond strength, one can optionally provide a further heat treatment of the particulate structure to obtain optimum bonding and coherency of the structure. Again, of course, one should avoid using temperatures in this optional step which exeed the heat-stability temperature of the organo-polymeric particles.

The liquid carrier in which the organo-polymeric particles and adhesives are formed into a stable dispersion is typically an aqueous liquid, although other liquid carriers such as various organic liquids may also be employed provided the heat-stable particles are insoluble in the carrier so that their particulate character is retained. In one preferred embodiment as described above, the adhesive is also insoluble in the carrier so that it may be dispersed among heat-stable particles as a discrete discontinuous phase within the dispersion, thereby aiding the avoidance of the formation of a substantial layer of the adhesive completely surrounding the particles. A partial listing of representative carrier liquids in addition to water, includes water miscible organic solvents, aqueous mixtures of water and water miscible organic solvents, and suitable water inmiscible organic solvents. Typical water miscible organic solvents include lower alochols, i.e., alcohols having 1 to about 4 carbon atoms in the alkyl group thereof; acetones, and ethers such as tetrahydrofuran. Typical water immiscible solvents includes lower alkyl esters, e.g. ethyl acetate, and halogenated organic solvents, e.g., halogenated hydrocarbons.

INTERACTIVE COMPOSITIONS

The particulate structures of the invention can advantageously contain one or more interactive compositions, although the presence of such compositions in the particulate structure is not required. These compositions contain one or more active components that undergo interaction with an analyte, or a reaction or decomposition product of the analyte, or with each other upon application of a liquid sample containing the desired analyte to an analytical element including the particulate structure. Such interaction can cause the release of a preformed detectable species within the element, the formation of a detectable species or otherwise produce a detectable change in the element. The term "interaction" is meant to refer to chemical activity, catalytic activity as in the formation of an enzyme-substrate complex, immunogenic activity as in an antigen-antibody reaction, and any other form of electrical, chemical or physical interaction that can release, produce, or otherwise provide within the element a detectable change that is directly or indirectly indicative of the presence and/or concentration of a desired analyte, or a reaction or decomposition product of the analyte.

Preferably (although not required), the detectable change that is produced is radiometrically detectable. Radiometric detection refers to detection by use of electromagnetic radiation measuring techniques such as fluorimetry, colorimetry, radioactive counting, phosphorimetry, and the like.

As will be appreciated, among the various components which can be present in interactive compositions are colorimetrically detectable dyes, pigments, and complexes; fluorimetrically detectable dyes, pigments and complexes; phosphorescent tags; radioactive tags; chemical reagents; immunoreagents such as antigens, haptens, antibodies, and antigen-antibody complexes, enzymes, and precursors and reaction products of the foregoing components. For further detail with respect to use of certain of these components, reference may be made to U.S. Pat. No. 3,992,158; Figueras, U.S. Ser. No.

877,193, filed Feb. 13, 1978; and Frank and Sundberg, U.S. Ser. No. 952,424, filed Oct. 18, 1978.

Although not required, the interactive compositions, if present in the particulate structure, can be immobilized therein to minimize or prevent undesired migration of the composition within the structure or other zones of an element containing the particulate structure. Immobilization can be effected by a variety of means including physical adsorption and chemical bonding to the heat-stable particles of the structure. For example, those heat-stable particles which are prepared from polymers containing an active linking or bonding site can advantageously be chemically bonded to one or more components of a particular interactive composition by establishing a covalent bond between this site and a reactive group of the interactive component. In addition to covalent bonding, ionic and hydrogen bonding can also be used where appropriate. In other cases, the molecular size or configuration of the interactive composition may be effective to physically entrap and immobilize a particular interactive composition in the particulate structure without use of any special physical adsorption or chemical fixing technique.

ELEMENT STRUCTURE

The elements of the invention containing the above-described particulate structure can have any one of a variety of different configurations. Certain preferred embodiments illustrating representative configurations of the element are described hereinafter, but it will be understood that other configurations of such elements although not specifically described are also considered within the scope of the invention.

In accord with one embodiment, an element of the invention comprises the above-described particulate structure optionally carried on a suitable support, preferably a radiation-transmissive support. In this configuration, assuming no support is present, the element contains simply the above-described particulate structure. This particulate structure provides a remarkably efficient liquid transport means and can be formed into a variety of shapes. In a typical embodiment, the structure is formed into a substantially coplanar configuration, for example, as a layer carried on a permanent or temporary support.

Figure 3:
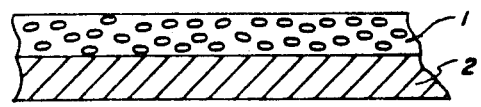
FIGS. 3-7 represent enlarged sectional views of certain preferred embodiments illustrating integral analytical elements containing a zone having the particulate structure characteristic of the invention as a layer which, if desired, can be superposed over a support or other contiguous zones in layer form.

FIG. 3 illustrates a representative element of the invention including the above-described particulate structure 1 carried on a suitable support 2. Where structure 1 has sufficient durability or in situations where durability requirements are not particularly critical or demanding, support 2 in FIG. 3 may be unnecessary. As will be apparent, the element of FIG. 3 can be used simply to transport a liquid by contacting the liquid and the element together. If desired, any one of a variety of interactive compositions may be present within particulate structure 1 of FIG. 3 to carry out one or more interactions between or among various analytes contained in the liquid.

Figure 4:
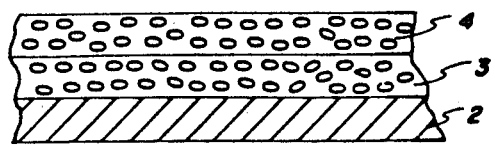

FIG. 4 illustrates another embodiment of an element containing at least two different zones, zone 3 and 4, carried on a support 2. Each of zone 3 and zone 4 represent a particulate structure of the invention. Two different zones 3 and 4 are present in the element of FIG. 4 to facilitate multiple treatments or operations on a particular liquid sample applied, for example, first to zone 4 from which it is transported by the particulate structure of zone 4 into zone 3 which is in fluid contact with zone 4. For example, the liquid sample can be sequentially exposed to two separate interactions or a series of sequential interactions by incorporating different interactive compositions in each of zone 3 and zone 4. Alternatively, or in addition, one can vary the average size of the organo-polymeric particles employed in each of zone 3 and zone 4. For example, if zone 3 has a smaller pore size or average void space than does zone 4, one can effectively trap or remove components contained in a liquid which have a physical size exceeding the pore size of zone 3 while permitting other smaller components to be transported through zone 4 into zone 3. In this manner a multi-zone element such as illustrated in FIG. 4 can be used to separate various liquid components, based on their physical size, into two or more distinct zones of the element.

Figure 5:
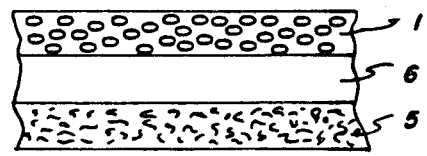

FIG. 5 illustrates yet a further embodiment of the element wherein the particulate structure is present as zone 1 of the element and zones 5 and 6 of the element represent other functional zones or layers. For example, zone 1 may be used as a spreading zone which meters and distributes an applied liquid sample to a separate reagent zone 5 containing one or more components of an interactive composition which, upon interaction with an analyte of the liquid, produces or releases a detectable product within the element. Such an element can optionally have present, as illustrated in FIG. 5, one or more intermediate zones between spreading zone 1 and reagent zone 5. Such intermediate zones can serve as adhesive or subbing layers to improve adhesion between spreading zone 1 and reagent zone 5, or as a radiation-blocking zone to block or screen any undesired background color or other optical interferent of zone 1 from the detectable product released or formed in zone 5. The use of such radiation-blocking zones is further illustrated, for example, in the multilayer analytical elements described in Clement, U.S. Pat. No. 4,042,335, issued Aug. 16, 1977. Or, intermediate zone 6 of FIG. 5 may represent a detectable species migration inhibiting layer such as described in Smith-Lewis and Figueras, U.S. Application Ser. No. 916,173, filed June 16, 1978, to inhibit or prevent undesired back-migration of detectable species formed in reagent zone 5 into spreading zone 1 where the detectable species may become masked or otherwise difficult to detect. Alternatively, intermediate zone 6 of FIG. 5 can represent a conventional non-fibrous isotropically porous spreading layer composed of, for example, a blushed polymer, a mixture of a blushed polymer and a particulate material, or a mixture of a polymeric binder and microcrystalline cellulose particles. Each of the foregoing conventional spreading layer compositions is more specifically described in the aforementioned U.S. Pat. No. 3,992,158.

Figure 7:
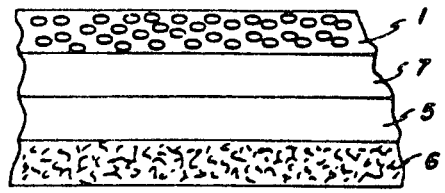
Figure 10:
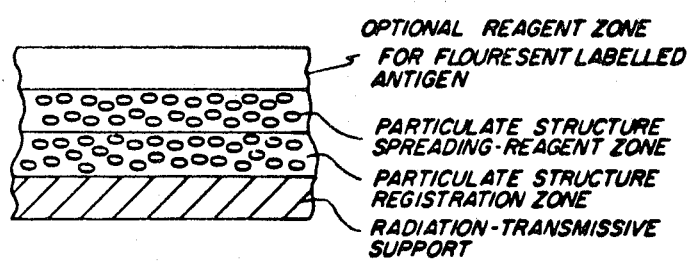
FIGS. 10-14 represent enlarged sectional views of various analytical elements particularly suited for immunoassay.

More than one intermediate zone 6 may be present in a multi-zone element of the type illustrated in FIG. 5. These zones may perform any one of a wide variety of functions, only some of which have been described herein. For example, the multi-zone element illustrated in FIG. 7 contains two intermediate zones 6 and 7, each of which can have any of a variety of functions. For example, zones 6 and 7 can each be a subbing zone; a radiation-blocking zone; a detectable product migration-inhibiting zone; a conventional non-fibrous, isotropically porous spreading zone; an additional reagent zone; or an additional particulate structure-containing zone of the type described in the present invention, and the like.

Figure 6:
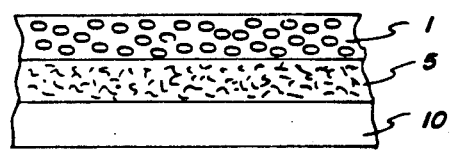

FIG. 6 represents another embodiment of the invention wherein the particulate structure is present as spreading zone 1 of the element. Reagent zone 5, as described above in FIG. 5, is present. Also present in fluid contact with zones 1 and 5 is registration zone 10 to receive reaction products or detectable species released or formed in the element. Registration zones such as zone 10 of FIG. 6 are further described in U.S. Pat. No. 4,042,335 and Figueras, U.S. Ser. No. 877,193 filed Feb. 13, 1978.

Figure 8:
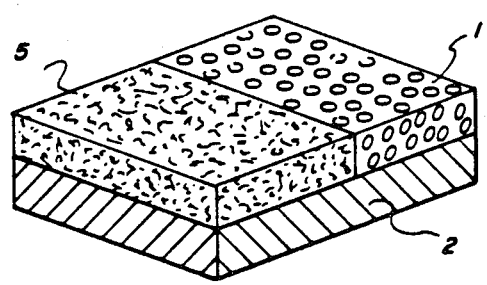
FIG. 8 represents an enlarged sectional view of a further embodiment illustrating a multi-zone analytical element having at least two adjacent abutting zones, at least one of these zones containing the particulate structure characteristic of the present invention.

FIG. 8 illustrates yet another embodiment of an element containing a particulate structure as described herein. This element is also a multi-zone element, but differs from previously illustrated multi-zone elements in that zones 1 and 5 of the element of FIG. 8 are adjacent abutting zones, such as a particulate structure spreading zone 1 and a reagent zone 5, rather than superposed layers as illustrated in the elements of FIGS. 5 and 6. An optional support 2 is also shown in the element of FIG. 8. Of course, as will be apparent, the element of FIG. 8 can have other zones in addition to zones 1 and 5 illustrated in FIG. 8, and each of these zones can represent a particulate structure of the invention, optionally having a different effective void or pore size. Or, the element can contain only one zone containing a particulate structure with each of the other optional zones having a different function and composition.

Figure 9:
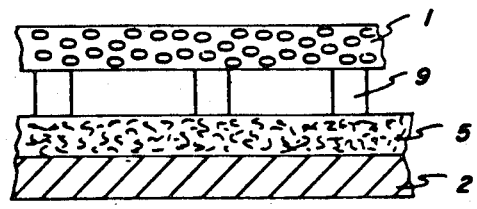
FIG. 9 represents an enlarged sectional view of another embodiment wherein an element of the invention contains at least two zones spaced apart from one another until the time of use of the element, at least one of these zones containing the particulate structure characteristic of the present invention.

FIG. 9 illustrates a further embodiment wherein an element contains at least two zones, e.g., zones 1 and 5 as described in FIG. 5, optionally carried on support 2, these zones initially being spaced apart by spacer means 9. Under conditions of use of the element, these zones are brought into contact such as by application of suitable compressive force to zone 1 of FIG. 9 which causes pressure-deformable spacer means 9 in FIG. 9 to deform and brings zone 1 into fluid contact with zone 5. Such a structure can be useful in an analytical element where, for example, two different interactive compositions are contained in zones 1 and 5 which would interact with one another prior to use of the element if zones 1 and 5 were maintained in physical contact.

As indicated above, various optional functional zones (or layers) and supports can be present in the multi-zone elements of the invention. Such optional zones can be located adjacent to the particulate structure of the invention or they can be superposed over or under the particulate structure. In addition to the specific functional zones discussed above, these optional zones can also include, among others, filtering zones to filter out or remove particular components of applied liquid samples, as described in U.S. Pat. 3,992,158; barrier compositions having a predetermined selective permeability to certain liquid components, analytes or interaction products of analyte, thereby permitting only selected species to come into fluid contact with particular zones of a multi-zone element, such barrier compositions being described in Bruschi, U.S. Pat. No. 4,066,403 issued Jan. 3, 1978; and zones including rupturable pod-like members which contain a liquid interactive composition as a reagent to be released into the element upon rupture of the pod-like member, such zones being described in Schaeffer, Minsk, and Stevens, U.S. Pat. No. 4,110,079, issued Aug. 29, 1978; and the like.

Methods of preparing and incorporating the above-noted zones in multi-zone elements of the invention are identical or similar to such methods as described in the foregoing U.S. patents and patent applications. Description of useful materials which can be employed to prepare such optional zones or layers are also provided in the foregoing patents and patent applications. Accordingly, the disclosures of the foregoing patents and patent applications are incorporated herein by reference and extensive description of such optional zones is unnecessary in the present specification.

Tyically, except for reflecting and radiation-blocking agents, zones or layers which may be present in elements of the invention, the various zones, supports, and other layers that may be present in an element of the invention are "radiation-transmissive". In the present specification the term "radiation-transmissive" refers to zones, supports, layers, and other materials in an element that permit effective passage of electromagnetic radiation used to detect an analytical change produced in the element. Such radiation can include visible light, fluorescent emission, radioactive radiation, X-ray radiation, and the like. The choice of a particular "radiation-transmissive" material in any given instance will depend upon the particular radiation selected for use with an element in which the material is to be incorporated. Of course, radiation-transmissive materials are not required in the present invention. In various embodiments one may choose to use radiation-blocking agents, zones, and layers to prevent radiation from interfering with certain chemical interactions occurring within an element of the invention, e.g., interactions involving radiation-sensitive materials.

As noted above, the various zones or layers of an analytical element of the invention are in "fluid contact" with one another. In the present specification the term "fluid contact" and similar terms refer to zones or layers of an element which are associated with one another in a manner such that, under conditions of use, a fluid, whether liquid or gaseous, can pass in the element between these layers or zones. Such fluid contact therefore refers to the capability of the element to permit passage of at least some components of a fluid sample between zones or layers of the element which are said to be in "fluid contact". Such fluid contact capability is preferably uniform along the contact interface between the fluid contacting zones. Zones which are in fluid contact can be contiguous, but they also may be separated by intervening zones or layers. Such intervening zones however will also be in fluid contact in this case and will not prevent the passage of fluid between the fluid contacting layers or zones. In many embodiments, zones or layers in fluid contact are contiguous with one another or separated by a mutually contiguous intervening zone prior to application of a liquid sample to the element. Nevertheless, in some circumstances it may be desirable to use initially spaced-apart zones or layers within an element as illustrated hereinabove in the element of FIG. 9. In such case, fluid contact between such spaced-apart zones is achieved substantially at the time of sample application, as by applying a compressive force to the element.

As previously mentioned, the elements of the invention can be self-supporting or carried on a support. Useful support materials include a variety of polymeric materials such as cellulose acetate, poly(ethylene terephthalate), polycarbonates, and polyvinyl compounds such as polystyrenes, glass or metallic supports, paper supports, and the like. A support of choice for any particular element will be compatible with the intended mode of result detection. For example, for fluorimetric detection wherein fluorimetric emission within the element is detected as the emission is transmitted from within the element through the support to an external detector, it is desirable to employ as a support material a material which exhibits a low degree of background fluorimetric emission. Thus, preferred supports include supports which are radiation-transmissive with respect to the particular radiation employed to provide detectable changes within the element. Thus, again, in the case of an element which provides a fluorimetrically detectable change, it is desirable to employ as a support, a material which transmits radiation at both the absorption and emission spectra of a fluorescent material used for result detection. In certain cases, it may also be desirable to have a support that transmits one or more narrow wavelength bands of radiation and is opaque to adjacent wavelength bands of radiation. This may be accomplished, for example, by impregnating or coating the support with one or more colorants or other opacifying agents having suitable absorption characteristics. Typically, when an element does include a support, the reagent zone, the reflecting or radiation-blocking zone, and the registration zone (if any one or more of the foregoing zones are present in the element), will usually, but not necessarily, be interposed in the element between the support and the particulate structure-containing layer or zone of the invention which often is the outermost layer or zone in the element. In general, the components of any particular layer or zone of an element of the invention, and the layer or zone configuration of the element, will depend on the particular use for which that element is intended.

In preparing multi-zone elements of this invention, the individual zones can be preformed and thereafter laminated prior to use or maintained as separate zones until brought into fluid contact when the element is placed in use. Zones preformed as separate members, if coatable, can advantageously be coated from solution or dispersion on a surface from which the zone can be physically stripped when dried. However, a convenient procedure which can avoid problems of multiple stripping and lamination steps when contiguous zones are desired, is to coat an initial zone on a stripping surface or a support, as desired, and thereafter to coat successive zones directly on or beside those previously coated. Such coating can be accomplished by hand, using a blade coating device or by machine using techniques such as "dip" or "bead" coating. For example, where the multi-zone elements represent elements bearing superimposed multiple layers, these multilayer elements can be coated using sequential coating techniques or using simultaneous multilayer coating methods and apparatus well known in the photographic art, such as, for example, the methods and apparatus described in U.S. Pat. Nos. 2,761,417, 2,761,418, 2,761,419 and 2,761,791. Use of simultaneous multilayer methods of coating is often advantageous in that it avoids the problem of "air-cratering" which can arise when layers are coated sequentially with a drying step between the coating of each successive layer. This problem results from the fact that as a layer is coated, the liquid medium in the coating composition enters the voids in the underlying layer and displaces air which ruptures the overlying layer and causes "pockmarks" or "craters" therein. Simultaneous multilayer coating is also advantageous in that it generally provides a substantial saving in the time and expense involved in the coating operation as compared to sequential techniques.

Slide-extrusion hoppers of the type described in U.S. Pat. No. 2,761,417 are often advantageous for simultaneous coating of a plurality of layers at least one of which is comprised of the organo-polymeric particles described herein. More particularly, a multilayer element can be coated by directing a coating composition containing the organo-polymeric particles through an extrusion slot of a slide-extrusion hopper and simultaneously flowing a layer of a second coating composition, which, if desired, may also contain organo-polymeric particles, down a slide surface of the slide-extrusion hopper. Preferably, the coating composition flowing through the extrusion slot is supplied at a volumetric flow rate that is substantially greater than the volumetric flow rate of the coating composition flowing down the slide surface. Also, it is desirable that the coating composition directed through the extrusion slot have a viscosity which is substantially higher than the viscosity of the coating composition flowing down the slide surface and a surface tension which is at least about as high and, most preferably, somewhat higher. Control of the coating parameters of flow rate, viscosity and surface tension in this manner aids in promoting the formation of discrete layers that are free from interlayer mixing and in avoiding the formation of repellency defects.

Elements of the present invention can be adapted for use not only in the field of clinical chemistry, but in chemical research and in chemical process control laboratories. In addition, the particulate structure of the invention can be associated with other functional zones or layers outside the field of analytical liquid analysis, e.g., layers or zones of photographic elements, to generally provide a resultant element having enhanced liquid transport capabilities. Analytical elements of the invention are well suited for use in clinical testing of body fluids, such as blood, blood serum and urine, because in this work a large number of repetitive tests are frequently conducted and test results are often needed soon after the sample is taken. In analyzing blood with the analytical element of this invention, the blood cells may first be separated from the serum, by such means as centrifuging, and the serum applied to the element. However, it is not necessary to make such separation. Whole blood can be applied directly to the element. The presence of blood cells on the element will not interfere with spectrophotometric analysis if it is carried out by reflection tecniques, with light being transmitted through the support and reflected from a radiation-blocking zone or other reflecting zone such that detecting radiation does not intercept the cells. Of course, if it is desired to directly observe the color of blood cells, such as in a direct hemoglobin analysis, no such reflecting layer is necessary. A particularly significant advantage of the integral analytical elements described herein is their ability to be used to analyze either serum, plasma, or whole blood.

As can be appreciated, a variety of different elements, depending on the analysis of choice, can be prepared in accordance with the present invention. Elements can be configured in a variety of forms, including elongated tapes of any desired width, sheets or smaller chips.

The prepared elements are placed in use by applying to the element a sample of liquid under analysis. Typically, an element will be formed such that an applied sample will first contact a zone having the described particulate structure to spread and transport the sample within the element, for example, to an adjacent or underlying reagent zone, if such a zone is present in the element. Because analytical accuracy of the present elements is not substantially diminished even though some variation in the volume of applied samples is encountered, sample application by hand or machine is acceptable. For reasons of convenience in detecting an analytical result, however, reasonable consistency in sample volume may be desirable.

In a typical analytical procedure using the present elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by the particulate structure, the element is exposed to any conditioning, such as heating, humidification or the like, that may be desirable to quicken or othewise facilitate obtaining any test result. If an automated procedure is used, it can also be desirable to have the particulate structure accomplish its liquid transport and spreading function within 20 to 30 seconds, preferably 20 seconds or less.

After the analytical result is obtained as a detectable change, it is measured, usually by passing the element through a zone in which suitable apparatus for reflection, transmission or fluorescence spectrophotometry, or scintillation counting is provided. Such apparatus would serve to direct a beam of energy, such as light, through the support. The light would then be reflected, such as from a radiation-blocking layer in the element, back to a detecting means or would pass through the element to a detector, in the case of transission detection. In a preferred mode, the analytical result is detected in a region of the element totally within the region in which such result is produced. Use of reflection spectrophotometry can be advantageous in some situations as it can effectively avoid interference from residues which may have left on or in the layers of the element. Conventional techniques of fluorescence spectrophotometry can also be employed if the detectable change produced in the element represents an increase or decrease in fluorescence. Detection would be accomplished using energy that excites a fluor and a detector that senses its fluorescent emission. Furthermore, when blood serum is tested, transmission techniques can be used to detect and quantify the released indicating ligands by directing a flow of radiant energy, for example, visible radiation, at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the detectable change produced in the element can be used. Various calibration techniques can be used to provide a control for the analysis. As one example, a sample of analyte standard solution can be applied adjacent to the area where the drop of sample is placed in order to permit the use of differential measurement in the analysis.

IMMUNOASSAY

This Section discusses a specific application of the particulate structure described herein, namely immunoassay. This application represents an especially preferred embodiment of the invention.

Immunoassay is a well-recognized technique for qualitative or quantitative assay of antibodies and antigens. The basis for all immunoassay techniques is the unique, immunological phenomena whereby a specific antibody recognizes and binds to a specific antigen. Immunochemical techniques offer advantages in terms of assay sensitivity because of the high affinity of antibody for its specific antigen. Therefore, in many instances immunoassay has made possible the detection of biological compounds that are present in trace quantities too low for traditional chemical and enzymatic techniques.

In general, immunoassay techniques can provide for a determination of the presence and/or concentration of either a specific antigen, a specific antibody, or a specific antigen-antibody complex. For example, given a known amount of antibody (or antigen), the level of its corresponding antigen (or antibody), sometimes referred to as its complement, can be determined. When the concentration of antigen (or antibody) is too small for direct measurement, a label (i.e., detectable species) can be affixed to a known fraction of the antigen (or antibody). This label, which is present and measurable at the requisite concentration, acts as a marker for the extent of antibody/antigen binding between the unknown antigen (or antibody) and its antibody (or antigen). The distribution of label between the bound and unbound antigen (or antibody) can then be used to calculate the amount of unknown that was present in a liquid test sample.

To accomplish the foregoing determination, may current immunoassay techniques require the physical separation of bound and unbound antigens (or antibodies); this is an additional step in the analysis which can be inconvenient and time consuming. In addition to this major drawback, most currently available techniques suffer from one or more of the following disadvantages: (a) Relatively large volumes (0.1–1.0 ml) of serum or other test liquid may be necessary compared to conventional chemical and enzymatic assays typically using 1.0–200 $\mu$l of liquid sample. (b) Time-consuming incubation (several hours or overnight) of the test mixture is required. (c) Many steps are necessary and must be performed individually and separately for completion of the assay (including sample addition, incubation, separation, quantitative of label). (d) Tests must often be run batchwise. (e) Adaptation to an automated system is difficult.

The use of an analytical element with a particulate structure as described above to conduct immunoassay overcomes many, if not all, of the above drawbacks. The basic principles of specific binding of antigen to antibody are embodied in these immunoassay elements; the preferred immunoassay elements as described hereinafter relying particularly on the competitive binding of a labelled and unlabelled antigen (or antibody) to its specific antibody (or antigen). It will be understood, however, that an immunoassay element comprising a particulate structure as described above can be made within the scope of the invention relying on basic principles of antigen-antibody interaction other than competitive binding. For example, an immunoassay based on an antigen-antibody displacement interaction as described in Figueras, U.S. Ser. No. 916,173 filed June 16, 1978 may be conducted with an immunoassay element comprising in one zone thereof a particulate structure and in association with that zone a labelled antigen-antibody (or antigen-labelled antibody) complex. The presence and/or concentration of an unknown antigen (or antibody) is determined by displacement of the labelled antigen (or labelled antibody) from the preformed labelled antigen-antibody (or antigen-labelled antibody) complex.

For illustrative purposes and for purposes of describing the currently preferred mode of immunoassay element comprising a particulate structure, the remainder of this Section is directed to an immunoassay element for the determination of the presence and/or concentration of an antigen based on the competitive binding of that unlabelled antigen and a labelled antigen to its antibody.

Thus, for example, a known amount of an antigen is rendered detectable, i.e., labelled, with a detectable species, such as with enzymes or fluorescent species or radioactive species. The antigen can be chemically linked or physically adsorbed to the detectable species. For example, a fluorescent species such as fluorescein can be covalently bonded to the antigen. In a preferred embodiment, a polymeric latex bead is "loaded" with a rare earth chelate, a fluorescent species, and the resultant rare earth chelate-loaded latex bead is employed as a fluorescent label to which the antigen of choice is physically adsorbed or covalently bonded. These latex polymer beads typically have an average diameter of from about 0.01 to about 0.2 micron and are "loaded" with up to about 7.5 weight percent of a rare earth chelate, preferably a europium or terbium chelate. Because of the large number of rare earth chelate molecules which can be loaded into a single latex bead, the resultant label is highly fluorescent and provides a fluorescent immunoassay exhibiting excellent sensitivity. Labelled antigen employing a fluorescent, rare earth chelate loaded polymeric latex bead as the label is described in Frank and Sundberg, U.S. Ser. No. 952,424, filed Oct. 18, 1978, and incorporated herein by reference.

In addition, an amount of the antibody for the labelled antigen is incorporated and immobilized in an analytical element, preferably within a zone thereof comprising a particulate structure. Such immobilization can be accomplished by adsorption or chemical bonding of the antibody to the surface of the organo-polymeric particles of the particulate structure. The liquid sample to be analyzed for unknown antigen is then contacted together with the element in the presence of the labelled antigen. The labelled antigen may be associated with the immunoassay element in one of several ways including, among others: direct addition of the labelled antigen to the liquid sample (containing unlabelled antigen) which is then applied to the immunoassay element for analysis; separate addition of the labelled antigen and the liquid sample to the immunoassay element, including addition of the labelled antigen just prior to or after addition of the liquid sample as well as addition of the labelled antigen to the element followed by drying and then rewetting the element upon addition of the liquid sample to be tested; or incorporation of the labelled antigen in the immunoassay element so that analysis can be initiated simply by application of the liquid sample to be tested. For example, the labelled antigen may be incorporated in a separate reagent zone of the element or in the same zone of the element containing the immobilized antibody. In any case, when the labelled antigen is incorporated in the element, care should be taken to maintain the labelled antigen apart from the immobilized antibody also in the element so that premature binding of labelled antigen to antibody is avoided.

When the liquid sample is contacted together with the immunoassay element in the presence of the associated, labelled antigen as noted above, the labelled antigen and the unlabelled antigen (present in the sample and representing the unknown to be determined) compete for binding to the antibody which is present immobilized in one zone of the element. Useful methods of measurement to determine the presence and/or concentration of unlabelled antigen which can then be employed include: (A) detecting the unbound, labelled antigen which has migrated into a second zone of the element, e.g., a registration zone, or (B) detecting the bound, labelled antigen which binds to the immobilized antibody. In either method, the amount of unlabelled antigen (i.e., the analyte) in the liquid sample can be determined based on the detected concentration of labelled antigen.

A partial listing of representative analytical elements illustrating various embodiments of an immunoassay element containing a particulate structure are presented hereinafter. Of course, as indicated above, other element configurations and other immunoassays may also be possible within the scope of the invention and therefore this listing is not exhaustive.

1. Fluorescence Immunoassay Element (FIA)

This embodiment, as shown in FIG. 9, comprises two superposed zones, each composed of a particulate structure of the invention, carried on a low fluorescence, radiation-transmissive support, e.g., a flexible plastic support such as one composed of polycarbonate, cellulose acetate, or polystyrene. The particulate structure-containing zone immediately over the support represents a registration zone. The particles of the registration zone are preferably spherical, organo-polymeric beads having a uniform size (i.e., they are monodisperse beads) within the range of from 5 to about 20 microns, most preferably about 6 to 8 microns, in diameter. Typical organo-polymers for the bead compositions of this zone are polymers 2 and 6 of Table I, preferably containing very low amounts of residual, unpolymerized styrene monomer, e.g., less than about 1% by weight (based on the dry polymer) of residual styrene. A preferred adhesive for this particulate structure is organo-polymer 1 of Table II. Preferably, a nonspecific protein such as ovalbumin, bovine serum albumin, gelatin, diluted nonimmune serum, etc., is adsorbed to the particles of the registration zone to minimize nonspecific binding in the final assay. In addition, this zone may optionally contain a highly reflective component, for example, from 1 to about 25 percent by weight of a pigment such as $TiO_2$ or $BaSO_4$. This amount of pigment can enhance light scattering within the registration zone, thereby effectively increasing the light available within the zone to excite a fluorescent-labelled species which migrates into this zone for detection. Viscosity modifying agents and surfactants may also be contained in this zone to facilitate its preparation as described hereinabove. A buffer can also be employed in this zone to maintain its pH, under conditions of use, between about 7 and 9. The upper zone represents a spreading/reagent zone and the particles in this zone also have a uniform size, preferably similar to that of the particles in the registration zone, and have antibody immobilized thereon, e.g., by adsorption or chemical bonding. This spreading/reagent zone may also contain a nonspecific protein as contained in the registration zone. The upper zone provides for uniform spreading of an applied liquid test sample, and the high surface-to-volume ratio of the particulate structure forming this zone gives excellent binding capacity. A pigment or dye can also be incorporated in some or all of the particles of this zone to serve as a radiation-blocking agent, i.e., a light screen, for a fluorescent species. A partial listing of representative such dyes or pigments includes Wachtung Red B Pigment ® (from E. I. duPont deNemours), Permanent Purple ® (from GAF), Sol Fast Methyl Violet ® (from Sherwin-Williams), Indofast Blue ® (from Harmon Colors), Regal 300 ® (from Cabot), Monolite Blue ® (from ICI), and Paliofast Blue ® (from BASF). The inclusion of a viscosity modifying agent and surfactant is optional. A buffer to maintain the spreading/reagent zone under conditions of use at a pH between 7 to about 10, preferably about 8.5, is typically present also. To carry out an immunoassay with this element, a fluorescent-labelled antigen may be associated with the element as mentioned earlier in this Section. For example, the labelled antigen may be incorporated in an optional reagent zone together with any necessary or desireable binder or applied to the element together with the liquid test sample. After applying the liquid test sample to the element in the presence of the associated, labelled antigen, the sample contacts the reagent/spreading zone of the element and the competitive binding interaction among the fluorescent-labelled antigen, the unlabelled antigen in the liquid test sample representing the analyte, and the immobilized antibody takes place. The unbound fluorescent-labelled antigen migrates into the registration zone where it can be quantitated through the clear plastic support by illuminating the zone with light at the excitation wavelength of the fluorescent label and measuring the emitted fluorescence. The radiation-blocking agent in the spreading/reagent zone hides the fluorescent label that remains bound to the immobilized antigen-antibody complex remaining therein.

2. Monolayer Fluorescence Immunoassay Element

Figure 11:
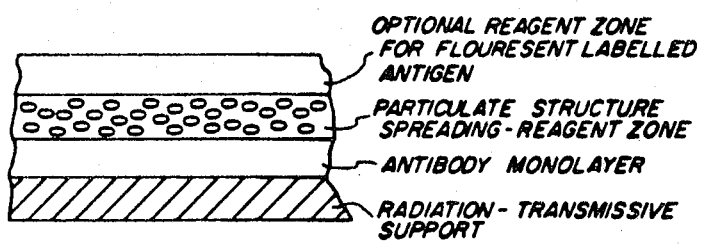

As shown in FIG. 11, another type of immunoassay element containing a particulate structure comprises a monolayer of antibody directly adsorbed to a plastic support similar to that used in FIA embodiment (1) above. This can be accomplished by incubating the plastic support with a solution of antibody (e.g., antiserum) diluted by a factor of from about 10 to 5000 (depending on the concentration of antibody in the antiserum and the range of the assay) for a period of several minutes to several hours, e.g., 0.5 minutes to 48 hours. The support can then be rinsed in saline and incubated in a nonspecific protein solution to minimize nonspecific binding in the assay. This second incubation step can be carried out in a time period similar to the first incubation step. The resultant support can then be rinsed in water and air-dried. The spreading zone is the same as the spreading/reagent zone for embodiment (1), except that no antibody is adsorbed in this zone. Labelled antigen may be associated with the element as in embodiment (1) above. In operation, the amount of labelled antigen bound to the adsorbed antibody is quantitated; the radiation-blocking agent in the upper spreading-/reagent zone hides the unbound labelled antigen.

3. Radioimmunoassay Element (RIA)

Figure 12:
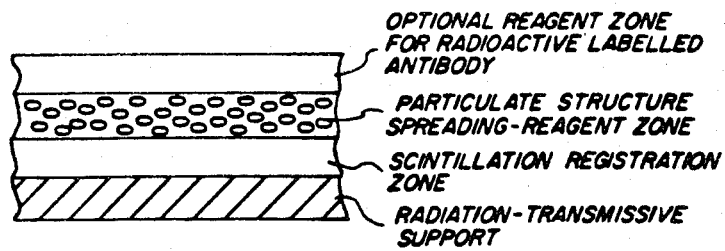

In the element shown in FIG. 12, a radiation-transmissive plastic support bears a scintillation zone as a registration zone which may be, for example, a solid latex scintillator layer as described in Chen, Miller and Perry, U.S. Pat. No. 4,127,499, issued Nov. 28, 1978, or, preferably, a particulate structure of the present invention comprising particles bonded with a fluor-imbibed latex adhesive. Illustrative fluor-imbibed latex adhesives include the scintillation fluors 2,5-diphenyloxazole and 2,2'-p-phenylenebis(5-phenyloxazole) imbibed into a latex form of one of the polymeric adhesives noted in Table II. Other components such as surfactants, viscosity modifying agents, buffers and the like as noted above may also be used in preparing this particulate structure. Over the scintillation zone is a spreading/reagent zone containing a particulate structure with antibody adsorbed to the particles thereof as in the FIA element of embodiment (1) above, except that no pigment is incorporated. The principles embodied in use of this immunoassay element are the same as in the FIA element of embodiment (1) above, except that the label is radioactive, rather than fluorescent. The unbound radioactive-labelled antigen is detected in the lower registration zone which is the solid equivalent of a "scintillation cocktail." Label in the upper spreading/reagent zone is not quantitated. This embodiment is particularly useful for the determination of very high molecular weight antigens because of its enhanced permeability and high counting efficiency.

4. Enzyme-Enhanced Immunoassay Element

Figure 13:
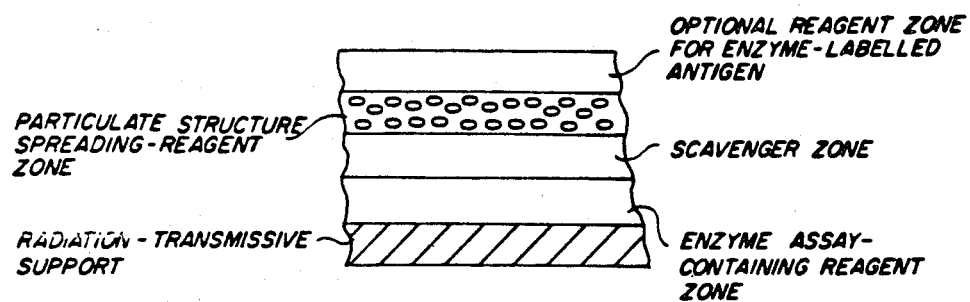

In this embodiment as shown in FIG. 13 above, the label is an enzyme. The radiation-transmissive plastic support is coated with a reagent zone containing portions of an interactive enzyme assay composition for the fluorometric, colorimetric or radioactive detection of an enzyme. This enzyme assay composition may be admixed in a film-forming vehicle such as gelatin, hardened gelatin, or agarose. For example, if the enzyme label is peroxidase, the enzyme assay composition may contain glucose, glucose oxidase (to generate peroxide from glucose) and a reduced dye precursor which is oxidized in the presence of peroxide and peroxidase, thereby producing a radiometrically detectable change in the element. The glucose portion of this enzyme assay composition can be located in a zone separate from the enzyme assay-containing reagent zone, for example, the spreading/reagent zone of FIG. 13, to avoid premature reaction of glucose with clucose oxidase. Or, the glucose portion could be separately added to the element or added together with the liquid test sample. At the time of use, the liquid test sample applied to the element causes the glucose to migrate into the enzyme assay-containing reagent zone to interact with the other components of the enzyme assay composition. Various surfactants can also be incorporated in this reagent zone composition to aid coatability. The optional scavenger zone of FIG. 13 prevents enzyme substrate, e.g. $H_2O_2$, generated in the enzyme assay-containing reagent zone from migrating up into the spreading/reagent zone where the enzyme labelled antigen, e.g., a peroxidase-labelled antigen, is present. As a result, only the unbound enzyme-labelled antigen that migrates into the enzyme assay-containing reagent zone is quantitated. Thus, where the enzyme label is peroxidase, the scavenger zone may contain a film-forming binder (such as gelatin), buffer, and catalase (catalase decomposes $H_2O_2$) to prevent migration of $H_2O_2$ generated in the enzyme assay-containing reagent zone into the spreading/reagent zone where it could react with peroxidase-labelled antigen that is bound to its immobilized antibody. The spreading/reagent zone is identical to that in the RIA element of embodiment (3) above, except that a portion of the interactive enzyme assay composition employed in the enzyme assay-containing reagent zone of the element may also be present in this zone, e.g., glucose as described immediately above. The enzyme-labelled antigen may be associated with the element by any of the previously mentioned techniques.

5. Fluorescence Immunoassay Element for Low-Molecular-Weight Antigens

Figure 14:
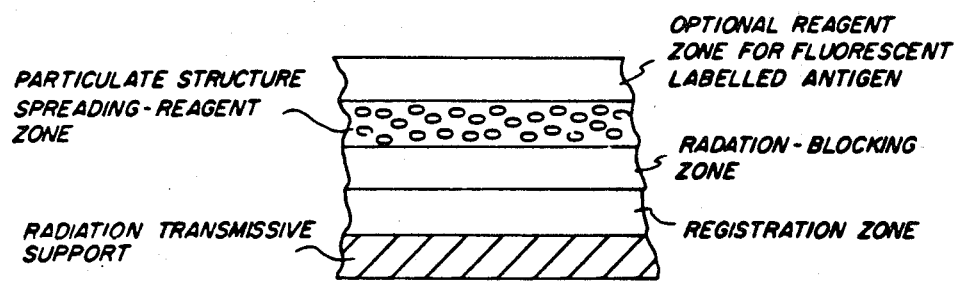

This modification of the FIA element of embodiment (1) above is illustrated in FIG. 14. The support is the same as that in embodiment (1). The registration zone is composed of a polymeric vehicle such as gelatin or agarose, and coating agents such as surfactants. Buffers or other components which might serve to enhance the fluorescence of the labelled antigen may be included in the registration zone. The radiation-blocking zone is similar in composition to the registration zone but contains a dye or pigment as a radiation-blocking agent to screen out the fluorescence of labelled antigen bound in the upper spreading/reagent zone. The spreading/reagent zone is the same as described for the FIA element of embodiment (1), except that the particles in the particulate structure of this zone may or may not be pigmented.

The following examples are presented to further illustrate certain embodiments of the present invention. In each of these examples numbers appearing in parentheses following a polymer name, e.g., (98:2), represent the parts by weight of the respective monomer components contained in the initial monomer blend from which the polymer was prepared.

EXAMPLE 1

Organo-Polymeric Bead Structure For Transport of Whole Blood

In this part of Example 1, three particulate aqueous transport layer structures were prepared and tested for whole blood transport capability. Two of these layer structures were control structures of the type specifically described in U.S. Pat. No. 3,992,158 and are outside the scope of the present invention. The third structure was an organo-polymeric particulate structure of the present invention. The two control layer structures were chosen on the basis of their demonstrated excellent performance as aqueous transport structures for blood serum. The first control layer structure tested was composed of a "blushed" cellulose acetate polymer layer containing $TiO_2$ particles. This particulate layer structure had a composition and was prepared in a manner similar to that described in detail in Example 3 of U.S. Pat. No. 3,992,158. The second control layer structure was composed of Avicel ® particles (microcrystalline cellulose particles purchased from FMC Corp.) dispersed in a binder polymer consisting of poly(vinyl pyrrolidone). This layer structure was coated from an aqueous coating mixture. The amount of microcrystalline cellulose particles contained in this layer structure (based on dry weight) was about 64.5 g/m² and the amount of poly(vinyl pyrrolidone) was about 1.6 g/m² (also based on dry weight). The approximate size of the microcrystalline cellulose particles in the second control structure was about 30 to 50 microns.

The third structure evaluated in this example was an organo-polymeric particulate layer of the present invention coated from a water dispersion having the following dry composition:

| | Coating Coverage |
|---|---|
| (i) 97.8 parts by weight of solid, spherical organo-polymeric beads of poly(styrene-co-divinylbenzene) (98:2) having a bead size of from about 35 to 75 microns | 196 g/m² |
| (ii) 2 parts by weight of a polymer adhesive composed of poly(n-butyl acrylate-co-styrene-co-2-acrylamido-2-methylpropane sulfonic acid) (70:20:10) | 4 g/m² |
| (iii) 0.2 part by weight of Surfactant 10G ® (p-nonyl phenoxy polyglycidol purchased from Olin Corp.) | 0.4 g/m² |

The polymer adhesive employed in the above-described composition was prepared as an aqueous latex having a 33.2 weight percent solids content consisting of the above-mentioned copolymer as a discontinuous phase and water as the continuous phase. This latex was preformed and then diluted 16.5X with water. A water dispersion containing the organic polymeric beads (i) and Surfactant 10G (iii) was then added to the adhesive latex and the resulting water dispersion was used to coat the above-described organo-polymeric bead structure. The wet coating thickness of the structure was about 530 microns. Subsequent to coating, the bead structure was air-dried at 54° C. The dry thickness of the resultant bead layer structure was about 370 microns.

Each of the three above-described layer structures was coated on a plastic film support of poly(ethylene terephthalate) bearing a thin film subbing layer to aid adhesion. The structures were then evaluated for whole blood transport capability by applying constant drop-size samples (~10 microliter drops) of whole blood to each structure and analyzing the ability of each structure to take up, uniformly distribute within itself, and rapidly transport the whole blood drop samples.

The results of this evaluation demonstrated that the organo-polymeric particulate structure of the present invention provided uniform and rapid transport of the blood drop samples. The red blood cells in these whole blood drop samples were rapidly taken up and uniformly distributed within the layer in approximately 10–20 seconds and the structure became uniformly pigmented. Moreover, spot size of the whole blood drop samples on the bead structure of the invention was uniform and reproducible, spot sizes of about 10 to 12 mm being obtained. Microscopic examination of this layer structure revealed an approximate mean void size of 25 microns.

In contrast, the control aqueous transport structures demonstrated substantially less effective whole blood transport capability. Typically a portion of the red blood cells were not taken up by control structures but were retained on the surface of the structure while the plasma was absorbed into the interior of the structure, or the blood cells were lysed by the structure and the resulting products of the lysis were taken up by the structure in an irregular manner as demonstrated by the non-uniform spot sizes and shapes produced by the whole blood drop samples on these control structures.

The results of this example demonstrate that the organo-polymeric particulate structures of the present invention are able to effectively and conveniently transport and accommodate aqueous samples containing such large and complex physiological species as red blood cells.

EXAMPLE 2

Organo-Polymeric Bead Structure For Whole Blood

An organo-polymeric particulate structure of the present invention was prepared in a manner similar to that described for the third layer structure in Example 1 above, except that the solid, spherical beads were about 65 to 120 microns in diameter and were composed of poly(styrene-comethacrylic acid) (98:2), and the structure was coated out of an aqueous dispersion. This bead structure was evaluated as in Example 1 for transport of whole blood and was also found to provide an extremely effective whole blood transport structure.

The organo-polymeric beads of this Example were prepared by bead polymerization as follows:

Bead Polymerization of Styrene and Methacrylic Acid

A. Materials: Styrene, methacrylic acid, potassium dichromate, and 2,2'-azobis(2-methylpropionitrile) (AIBN) were used. In addition, colloidal silica was used as obtained from DuPont either as a 30 or 40 percent solution with the trade name Ludox HS30 or Ludox HS40. A surface active agent was also used consisting of a condensation copolymer of adipic acid and diethanol amine prepared by heating the monomers neat, in a beaker equipped with a magnetic stirring bar, on a hot plate until a centipoise reading of 12,000 to 350,000 was obtained using a Brookfield viscometer, Model LVT, 24° C., 3–0.6 RPM, and a number 4 spindle.

B. Procedure:

1. Aqueous Phase:

Water (600 g), Ludox HS30 (90 g), diethanolamineadipic acid copolymer (15 g of a 10% aqueous solution), and potassium dichromate (6 g of a 2.5% aqueous solution) were placed in a 2000 ml brown bottle, and the pH adjusted to 4 with a 1 N hydrochloric acid solution.

2. Organic Phase:

Styrene (588 g), methacrylic acid (12 g), and AIBN (6 g) were placed in a flask and stirred until the initiator had dissolved.

3. Dispersion:

The organic phase was dispersed in the aqueous phase (with cooling) by a Brinkman Polytron homogenizer (purchased from Brinkman Instruments Company); 115 volts, 5 amps, and 60 Hz, for 2 minutes at a setting of 5. Auxiliary stirring with a Lightnin mixer (purchased from Lightnin Company) was required to obtain a uniform dispersion. The brown bottle was capped, sealed with tape, allowed to remain at ambient temperature without agitation for one hour to effect limited coalescence, and finally placed in a 60° C. bath overnight.

The following day the brown bottle was removed from the bath, allowed to cool, the reaction mixture stirred to redisperse settled beads, strained through a fine mesh screen, and collected on 230 Reeve Angel filter paper (purchased from Reeve Angel Company). The beads were redispersed in water three times, collected after each redispersal, and air dried after the final redispersal. The dried beads were put through a 100 mesh sieve to remove any large particles that were present.

EXAMPLE 3

Multi-Zone Organo-Polymeric Bead Structures For Whole Blood Transort and Red Cell Separation In this example, a multi-zone element of the type illustrated in FIG. 4 is demonstrated as follows:

A poly(ethylene terephthalate) film support bearing a thin adhesive subbing layer was overcoated with two, superposed organo-polymeric bead structures (i.e. layers) of the present invention. The structures differed with respect to the size of the beads used in the structures. The bead structure immediately adjacent the subbing layer of the film support consisted of a bead structure similar to that described in Example 2, except that the poly(styrene-co-methacrylic acid) beads were about 6 microns in diameter. A second bead structure was then coated over this first bead structure. The second bead structure was identical to that described in Example 2. The multi-zone element of this example was then tested for its blood transport capability. It was found that the top layer containing the large beads readily took up and uniformly distributed the whole blood drop samples applied to it as evidenced by the uniform coloration formed in the top layer at the site of contact with the whole blood drop sample. The lower bead layer (containing the 6 micron beads) rapidly became wetted with colorless portions of the whole blood sample but did not take up any of the red blood cells as evidenced by the fact that it was a clear layer and remained so, even after evaporation of the fluid portion of the whole blood drop samples. This example demonstrates the capability of organo-polymeric bead structures to be used in a multi-zone analytical element to separate components of an aqueous liquid into two or more distinct zones based on the molecular size and configuration of the components.

EXAMPLE 4

Multi-Zone Element For Determination of Whole Blood or Plasma Glucose Using Organo-Polymeric Bead Transport Structure In this example, a multi-zone element for determination of whole blood or plasma glucose was prepared. The element was a multi-zone element of the type illustrated in FIG. 7. The element had a transparent poly(ethylene terephthalate) film support bearing a thin adhesive subbing layer overcoated with the following layers (listed in order beginning with the layer immediately adjacent the aforementioned subbing layer):

(i) Color-forming enzymatic glucose reagent layer containing glucose oxidase (24,000 U/m$^2$), 4-aminoantipyrene hydrochloride (0.86 g/m$^2$), 1,7-dihydroxynaphthalene (0.65 g/m$^2$), peroxidase (18,000 U/m$^2$), 5,5-dimethyl-1,3-cyclohexanedione (0.22 g/m$^2$), 6-amino-4,5-dihydroxy-2-methylpyrimidine (0.02 g/m$^2$), deionized gelatin (16 g/m$^2$), and 3,3-dimethylglutaric acid (1.96 g/m$^2$) as buffer to maintain pH of reagent layer at 5.0 when the element is spotted with drop of whole blood;

(ii) Subbing layer containing poly-n-isopropylacrylamide (0.32 g/m$^2$);

(iii) Radiation blocking-reflecting layer containing TiO$_2$ (18 g/m$^2$), Triton X-100, an octylphenoxy polyethoxy ethanol available from Rohm and Haas Co., (1.08 g/m²) and poly(acrylamidecoethyl acryloylacetate) (90:10) (10.8 g/m²) and (iv) Organo-polymeric bead structure to spread whole blood sample hav ing a layer structure identical to that described in Example 2. Calibration curves for the above-described multi-zone element were then generated by spotting commercially available serum calibrator solutions containing from 0 to 400 mg glucose/dl. on the element, incubating the element for 12.5 minutes at 37° C., and thereafter detecting the color density produced in the color-forming reagent layer by reflection spectrophotometry through the transparent poly(ethylene terephthalate) film support. Two serum control fluids and a whole blood sample, each containing an unknown glucose level, were then spotted on separate but identical samples of the element and the glucose levels were determined on each of these element samples by use of the previously generated calibration curves. The glucose levels of these unknowns were also determined by accepted reference methods. Good agreement was obtained between the glucose values predicted by the multi-zone element and those obtained by the reference method as shown in Table III below:

TABLE III

| Sample Tested | Reference Glucose Level (mg/dl) | Glucose Level Predicted By Multi-zone Element (mg/dl) |
|---|---|---|
| Serum Control Fluid (1) | 89.8 | 94 |
| Serum Control Fluid (2) | 276 | 267 |
| Whole Blood Sample | 96 | 93 |

EXAMPLE 5

Organo-Polymeric Bead Structure As a Transport And Regent-Containing Structure

In this example, an element for the analysis of serum glucose was prepared. The element contained a single organo-polymeric bead structure which also included an interactive composition containing all the necessary colorforming and enzymatic reagents to perform a quantitative serum glucose assay. The bead structure was carried on a poly(ethylene terephthalate) film support bearing a thin adhesive subbing layer. The element was prepared as follows- Materials For Organo-Polymeric Bead Structure (i) Beads—Poly(styrene-co-vinylbenzyl chloride-co-methacrylic acid) (78:20:2);

(ii) Adhesive—Poly(n-butyl acrylate-co-styrene-co-2-acrylamido-2-methylpropane sulfonic acid) (76:19:5);

(iii) Glucose oxidase—206 units/mg. Lot No. 58 (Miles Laboratories);

(iv) Peroxidase—1000 units/mg (horseradish) obtained from Miles Laboratories (Cat. No. 38–444);

(v) Triton X-100—Octylphenoxypolyethoxy ethanol obtained from Rohm and Haas Co. and (vi) Chromogen—2-(3-bromo-5-methoxy-4-hydroxyphenyl)-4,5-bis(4-methoxyphenyl)imidazole.

Preparation Of Bead-Enzyme Slurry 20 g of beads were added to 100 ml phosphate buffer solution, pH 7.4. 5 ml of glucose oxidase (containing 30 mg of protein) and 30 mg (30,000 units) of peroxidase were added. The mixture was stirred overnight at room temperature and washed on a filter funnel with 1000 ml of 0.15 N sodium chloride.

Preparation of Element

The subbed poly(ethylene terephthalate) support was coated with the bead slurry described above (162 g/m²), adhesive (3.24 g/m² added as a 33.2% aqueous dialyzed latex), Triton X-100 (0.4 g/m²) and chromogen (1.6 g/m²). The element was buffered to pH 5.9 with NaH$_2$PO$_4$.

The element was tested, qualitatively, by spotting 10 microliters of serum glucose standards containing 0. 15, 30, 60 and 125 mg/dl respectively, and Interstate Blood Bank serum calibrators (levels, 1, 3, 7 and 8) and incubating at 37° C. for 10 minutes. Results demonstrated good differentiation between each of the levels of glucose tested.

EXAMPLE 6

Organo-Polymeric Bead Structure For Direct Hemoglobin Analysis

It is known that the blood protein hemoglobin (Hb) can be assayed directly by analyzing spectrophotomerically a dried sample of whole blood spotted onto an absorbent matrix. Such a direct Hb assay is typically carried out by evaluating the 540 nm absorption peak of Hb. Although it is known that several different forms of hemoglobin exist, such as carboxy-hemoglobin, met-hemoglobin, or sulf-hemoglobin, which do not exhibit an absorption peak at 540 nm, only minor amounts of such hemoglobin derivatives are generally present in whole blood. For example, the total Hb content of whole blood typically is composed of over 95 weight percent of oxy-hemoglobin having an absorption peak at 540 nm and less than 5 weight percent of other forms of Hb having absorption peaks at points in the visible spectrum other than 540 nm. Thus, an accurate total HB assay can be performed merely by examining the 540 nm absorption band of a whole blood sample and adjusting the result obtained by a standardized quantity to allow for the presence of minor amounts of other forms of Hb. Of course, this can be effective only if one has a suitable absorbent matrix on which to spot whole blood samples. Such a matrix should rapidly take up a sample drop of whole blood applied thereto, hemolyze the red blood cells contained in the blood so that the Hb content of the cells is released, and uniformly distribute the products of the lysis throughout the matrix in the form of a spot pattern exhibiting a regular and reproducible shape and size. The dried spot pattern should show little or no irregularities and nonlinearities in color distribution across its surface area. Preferably, the absorbent matrix sould perform the complete operation of whole blood hemolysis and spreading within itself in a matter of seconds so that the Hb assay can readily be performed without delay. In this regard the organopolymeric bead structures of the present invention have been found to represent an excellent absorbent matrix for preforming Hb assays. A typical bead structure of the invention for such a direct Hb analysis had a composition and was prepared in a manner identical to that described in Example 2, except that Surfactant 10G was replaced by an amount of Triton X-100 adjusted to provide 1 weight percent of Triton X-100 in the bead structure (as measured on a dry weight basis) and the amount of the polymer glue contained in the bead structure was adjusted to 3 weight percent (also as measured on a dry weight basis). Triton X-100 was used to enhance hemolysis of the red blood cells. The "spread time" required for this bead structure, i.e., the time required for it to take up, lyse the red blood cells and achieve uniform distribution of the lysis products throughout the structure was about 18 seconds. Even faster spread times of about 7–9 seconds was obtained using an organo-polymeric bead structure similar to that described above, except that the beads were prepared from a copolymer of poly(styrene-co-divninylbenzene) (98:2) as described in Example 1 having a bead diameter of from about 35 to 75 microns.

EXAMPLES 7–49

Alternative Organo-Polymeric Bead Structures

A series of effective liquid transport elements were prepared in a manner similar to that described in Example 1, except that the organo-polymeric beads, the adhesive, and surfactant were varied as indicated in Table IV below. Elements 8–36 and 46 of Table IV are examples of elements as illustrated in FIG. 3 having a single layer of particulate structure carried on a support.

Elements 37–45 and 47–49 of Table IV are examples of elements as illustrated in FIG. 4 having a first particulate structure layer 3 on a support 2 overcoated with a second particulate structure layer 4.

TABLE IV

| Example | Beads[1] | Amount (g/m$^2$) | Adhesive[1] | % Amount[2] | Liquid Carrier[3] | % Surfactant[4] | Support[5] |
|---|---|---|---|---|---|---|---|
| 8 | 5 | 43.0 | 16 | 4 | H$_2$O | 10G - 0.025 | A |
| 9 | 5 | 43.0 | 12 | 2 | H$_2$O | 10G - 0.025 | A |
| 10 | 5 | 64.6 | 1 | 0.5 | H$_2$O - pH 8.2 | 10G - 0.025 | A |
| 11 | 5 | 43.0 | 18 | 5 | H$_2$O | 10G - 0.025 | A |
| 12 | 5 | 43.0 | 19 | 5 | H$_2$O | 10G - 0.025 | A |
| 13 | 5 | 43.0 | 15 | 3 | H$_2$O | 10G - 0.025 | A |
| 14 | 5 | 43.0 | 7 | 5 | H$_2$O | 10G - 0.025 | A |
| 15 | 5 | 43.0 | 13 | 3 | H$_2$O | 10G - 0.025 | A |
| 16 | 5 | 43.0 | 24a | 5 | H$_2$O | 10G - 0.025 | A |
| 17 | 5 | 43.0 | 17 | 2 | 15% MeOH pH 8.3 | 10G - 0.025 | B |
| 18 | 5 | 43.0 | 3a | 1 | 1% MeOH | None | C |
| 19 | 5 | 64.6 | 1 | 2 | 10% MeOH | 10G - 0.025 | C |
| 20 | 5 | 43.0 | 3b | 3 | 10% MeOH | None | C |
| 21 | 2 | 43.0 | 11 | 4 | H$_2$O | 10G - 0.025 | A |
| 22 | 2 | 43.0 | 8 | 5 | H$_2$O | 10G - 0.025 | A |
| 23 | 2 | 43.0 | 21 | 5 | H$_2$O | 10G - 0.025 | A |
| 24 | 2 | 86.0 | 24b | 5 | H$_2$O | 10G - 0.025 | A |
| 25 | 2 | 43.0 | 12 | 3 | H$_2$O | 10G - 0.025 | A |
| 26 | 2 | 43.0 | 24a | 3 | H$_2$O | 10G - 0.025 | A |
| 27 | 2 | 43.0 | 10 | 5 | H$_2$O | 10G - 0.025 | A |
| 28 | 2 | 43.0 | 9 | 5 | H$_2$O | 10G - 0.025 | A |
| 29 | 2 | 43.0 | 3a | 5 | H$_2$O | 10G - 0.025 | A |
| 30 | 2 | 43.0 | 13 | 5 | H$_2$O | 10G - 0.025 | A |
| 31 | 2 | 43.0 | 21b | 5 | H$_2$O | 10G - 0.025 | A |
| 32 | 12 | 43.0 | 24b | 3 | H$_2$O | None | A |
| 33 | 12 | 43.0 | 24b | 5 | H$_2$O | 10G - 0.025 | A |
| 34 | 12 | 43.0 | 11 | 5 | H$_2$O | None | A |
| 35 | 13/TiO$_2$ | 43.0/10.8 | 1 | 4 | 10% MeOH | 10G - 0.025 | C |
| 36 | 14 | 43.0 | 1 | 2 | H$_2$O - pH 8.5 | 10G - 0.025 | A |
| 37 1st Layer | 2A/TiO$_2$ | 32.3/15 | 1 | 2 | 24% MeOH pH 8.5 | Z - 0.01 | A |
| 37 2nd Layer | 2 | 43.0 | 1 | 2 | 24% MeOH pH 8.5 | Z - 0.017 | — |
| 38 1st Layer | 2 | 43.0 | 1 | 2 | 24% MeOH pH 8.5 | Z - 0.017 | A |
| 38 2nd Layer | 2A/TiO$_2$ | 32.3/15 | 1 | 2 | 24% MeOH pH 8.5 | Z - 0.01 | — |
| 39 1st Layer | 2A | 43.0 | 1 | 2 | 27% MeOH pH 8.5 | Z - 0.017 | D |
| 39 2nd Layer | 2/TiO$_2$ | 32.3/15 | 1 | 2 | 27% MeOH pH 8.5 | Z - 0.017 | — |
| 40 1st Layer | 2/TiO$_2$ | 32.3/15 | 1 | 2 | 27% MeOH pH 8.5 | Z - 0.017 | D |
| 40 2nd Layer | 2A | 43.0 | 1 | 2 | 27% MeOH pH 8.5 | Z - 0.017 | — |
| 41 1st Layer | 2B | 43.0 | 1 | 2 | 27% MeOH pH 8.5 | Z - 0.017 | D |
| 41 2nd Layer | 2/TiO$_2$ | 32.3/15 | 1 | 2 | 27% MeOH pH 8.5 | Z - 0.017 | — |
| 42 1st Layer | 2/TiO$_2$ | 32.3/15 | 1 | 2 | 27% MeOH pH 8.5 | Z - 0.017 | D |
| 42 2nd Layer | 2B | 43.0 | 1 | 2 | 27% MeOH pH 8.5 | Z - 0.017 | — |
| 43 1st Layer | 2C/TiO$_2$ | 32.3/10.8 | 1 | 2 | 34% MeOH pH 8.5 | Z - 0.05 | D |
| 43 2nd Layer | 2/TiO$_2$ | 32.3/15 | 1 | 5.2 | 34% MeOH pH 8.5 | Z - 0.1 | — |
| 44 1st Layer | 5 | 43.0 | 1 | 3 | 10% MeOH pH 8.1 | 10G - 0.05 | C |

TABLE IV-continued

| Example | Beads[1] | Amount (g/m$^2$) | Adhesive[1] | % Amount[2] | Liquid Carrier[3] | % Surfactant[4] | Support[5] |
|---|---|---|---|---|---|---|---|
| 44 2nd Layer | 2C | 43.0 | 1 | 3 | 10% MeOH pH 8.1 | 10G - 0.05 | — |
| 45 1st Layer | 2C/TiO$_2$ | 32.3/15 | 1 | 2 | 50% MeOH pH 8.3 | 10G - 0.05 | C |
| 45 2nd Layer | 2 | 32.3/10.8 | 1 | 3 | 40% MeOH pH 8.3 | 10G - 0.05 | — |
| 46 | 2 (20–65 μm) | 86.1 | 1 | 3 | H$_2$O | TX - 1.0 | A |
| 47 1st Layer | 2 | 64.6 | 2 | 3 | H$_2$O - pH 8.0 | TX - 0.8 | E |
| 47 2nd Layer | 2C | 86.1 | 2 | 3 | H$_2$O - pH 8.0 | TX - 1.0 | — |
| 48 1st Layer | 2 | 64.6 | 2 | 3 | H$_2$O - pH 0.8 | TX - 0.8 | E |
| 48 2nd Layer | 2C/15 | 73.2/13 | 2 | 3 | H$_2$O - pH 7.8 | TX - 1.0 | — |
| 49 1st Layer | 2 | 64.6 | 2 | 3 | H$_2$O - pH 8.0 | TX - 0.8 | E |
| 49 2nd Layer | 2C/16 | 81.8/4.3 | 2 | 3 | H$_2$O - pH 7.8 | TX - 1.0 | — |

[1]The numbers of the polymers in Tables I and II are used to designate the polymers that make up the beads and adhesives, respectively. The letters indicate that a dye or pigment is also incorporated in the polymer beads as follows:
A = 2% of Permanent Purple based on the weight of the beads.
B = 2% of Regal 300 Carbon based on the weight of the beads.
C = 1.5 to 2% of Wachtung Red based on the weight of the beads.
the size ranges of the beads are given in μm when the size is larger than 1 to 10 μm.
[2]The amount of adhesive employed is given as weight percent based on the weight of the beads.
[3]With two exceptions, those examples which specify a pH were buffered by incorporation of boric acid and potassium chloride into the coating composition and adjustment with ammonium hydroxide, in sufficient amount to produce, when coated, a coverage of 0.136 g/m$^2$ of boric acid and 0.168 g/m$^2$ of potassium chloride. The two exceptions- the second layers of Elements No. 48 and 49, were buffered by incorporation of disodium hydrogen phosphate and citric acid in the coating composition to a concentration of 0.1M before adjustment of the coating composition with ammonium hydroxide. Those examples where no pH is specified were not buffered.
[4]The surfactants employed, where specified, are:
10G = Surfactant 10G, a nonylphenoxypolyglycidol sold by Olin Corp.
Z = Zonyl FSN, a fluorochemical surfactant sold by E. I. du Pont Co.
TX = Triton X-100, an octylphenoxypolyethoxyethanol sold by Rohm and Haas Co.
The amounts of surfactant specified are weight percents based on the total coating composition.
[5]The supports on which the particulate structures were coated were:
A - Poly(ethylene terephthalate) bearing a thin adhesive subbing layer as described in U.S. Pat. No. 3,143,421; which subbing layer, in turn, bears a thin gelatin layer.
B - A support bearing a layer composed of a scintillation counting composition prepared from a loaded latex coating composition prepared essentially as described in Example 1 of U.S. Pat. No. 4,127,499, issued November 28, 1978, except that no gelatin was used, the organic solvent for the fluors was a 6:1 volume mixture of methanol:acetone, and the latex employed was a 34.6 percent solids latex of poly(n-butyl acrylate-co-styrene-co-2-acrylamido-2-methylpropanesulfonic acid) (Weight Ratio 20/75/5). The final dispersion had a 43.8 percent solids content, weighed 3,850 g, and was prepared from:
2,164 g H$_2$O
1,264 g Polymer latex
420 g 2,5-diphenyloxazole (a fluor)
2.0 g 2,2'-p-phenylenebis(5-phenyloxazole)[a fluor]
The coverage of the scintillation counting composition on the support was 108 g/m$^2$. The support itself was poly(ethylene terephthalate) bearing a thin adhesive gel subbing layer.
C - Lexan ® polycarbonate purchased from General Electric Company
D - Lexan ® polycarbonate bearing a thin adhesive subbing layer composed of a mixture of one part gelatin and two parts of poly(acrylonitrile-co-vinylidene chloride-co-acrylic acid) (Weight Ratio 15/8/77).
E - Trycite ®, a polystyrene sold by Dow Chemical Co., bearing a thin adhesive subbing layer as described in U.S. Pat. No. 3,143,421; which subbing layer, in turn, bears a thin gelatin layer.

EXAMPLE 50

Fluorescence Immunoassay Element

A. Element Preparation

In this example a fluorescence immunoassay element representing embodiment 1 as described in the Immunoassay Section was prepared.

1. Spreading/Reagent Zone Dispersion:

An aqueous dispersion was prepared containing 46% (wt. %) microbeads adsorbed with the antibody antibovine gamma globulin (Anti-BGG); 0.5% (wt. %) of the non-ionic surfactant Zonyl FSN ® (purchased from duPont); 2.5% (wt. %) polymeric adhesive No. 3 of Table II: and 2% (wt. %) normal rabbit serum as nonimmune serum. The dispersion was buffered to pH 8.5 with a mixture of H$_3$BO$_3$ and KCl. The viscosity of the dispersion, as determined by a Brookfield viscometer at 60, 30 and 12 rpm and room temperature, was 33 CP, and the surface tension of the dispersion was 24.9 dynes/cm$^2$. The microbeads used in the aforementioned dispersion contained encapsulated Paliofast Blue ® as a radiation-blocking agent, had an average particle size of 6 to 8 microns, and were composed of polymer No. 2 of Table I. The amount of Paliofast Blue ® pigment encapsulated by the microbeads was about 1.5 wt. % of the beads. Pigment encapsulation was achieved by incorporating the pigment into the Organic Phase of the bead polymerization described above in Example 2. Anti-BGG was adsorbed to the above-described microbeads by the following procedure: The beads were washed with 0.15 M NaCl to thoroughly clean the bead surface and then dried by suction filtration and resuspended at 20 wt. % solids in a solution containing 99 parts by volume of 0.03 M Na$_2$CO$_3$, pH 9.5, and 1 part by volume of Anti-BGG rabbit serum. The bead suspension was stirred at room temperature for 24 hours and centrifuged for 10 min. at 6000 rpm to collect the beads. The beads were washed with 0.15 M NaCl and then centrifuged again.

2. Registration Zone Dispersion:

An aqueous dispersion was prepared containing 46% (wt. %) microbeads adsorbed with normal rabbit serum, the microbeads having an average particle size of 6 to 8 microns and composed of polymer No. 1 of Table I; 2.5% (wt. %) of polymeric adhesive No. 3 of Table II; and 0.2% (wt. %) of the non-ionic surfactant Zonyl FSN ®. The dispersion was buffered as in (1) above. The viscosity of the dispersion was 22 CP, and the surface tension was 29.5 dynes/cm$^2$.

3. Coating Procedure

The immunoassay element was then prepared by coating as follows: A transparent polystyrene plastic film support exhibiting a low level of fluorescence was coated with 80 g/m$^2$ of the registration zone dispersion and 28 g/m$^2$ of the spreading/reagent zone dispersion using the multiple slide-hopper bead coating technique described above in the Element Structure Section.

B. Analysis

A 10 μl droplet of aqueous test solution buffered to a pH of 7.4 and containing $5 \times 10^{-8}$ M fluorescein-labelled bovine gamma globulin as the labelled antigen and a varying level of unlabelled bovine gamma globulin as the unlabelled antigen ranging from 0 to $10^{-5}$ M was applied to a series of the immunoassay elements described in Part A. The buffer contained in the aqueous test solution was composed of 50% normal rabbit serum and 50% phosphate buffered saline (0.15 N saline, 0.01 M sodium phosphate). The 10 μl droplet of test solution was readily taken up, i.e., spread, by the spreading/reagent zone in about 25 seconds. Thereafter the element was incubated for 15 minutes at 37° C. A reflectance fluorimeter having excitation and emission filters at 490 and 515, respectively, was then used to obtain the data shown in Table V. The fluorimeter was set up to direct a beam of light of the excitation wavelength of 490 nm through the polystyrene support of the element into the registration zone to detect fluorescence produced in this zone by the unbound labelled bovine gamma globulin which had migrated into the zone. These fluorescence levels were then correlated to the varying levels of unlabelled antigen which were known to be present in the 10 μl of aqueous test droplets. As can be seen from the response data in Table V, these immunoassay elements produced a readily detectable change in fluorescence response corresponding to the varying levels of unlabelled antigen contained in the aqueous test droplets.

TABLE V

| CONCENTRATION UNLABELLED BOVINE GAMMA GLOBULIN | MEASURED FLUORESCENCE (ARBITRARY UNITS) |
| --- | --- |
| 0 | 385 |
| $2.5 \times 10^{-8}$M | 388 |
| $5 \times 10^{-8}$M | 431 |
| $1 \times 10^{-7}$M | 466 |
| $2 \times 10^{-7}$M | 491 |
| $1 \times 10^{-6}$M | 540 |
| $1 \times 10^{-5}$M | 553 |
| Buffer blank | 40 |

The invention has been described in detail with particular reference to certain preferred embodiments thereof, but it will be understood that variations and modifications can be effected within the spirit and scope of the invention.

We claim:

1. In a method of making an element for the analysis or transport of a liquid, said element containing a support bearing a particulate structure, said method comprising:
   (a) forming in a liquid carrier a stable dispersion of
      (i) a plurality of heat-stable, organo-polymeric particles non-swellable in and impermeable to said liquid under analysis, said particles having a particle size of from about 1 to 200 microns, and
      (ii) an adhesive, in an amount less than 10 percent by weight of said particles, comprising an organic polymer, said adhesive polymer being different from that of said particles and being insoluble in said liquid under analysis; and
   (b) applying said dispersion to said support and removing said liquid carrier at a temperature below the heat-stability temperature of said particles to concentrate said adhesive at contiguous surface areas of adjacent particles and bond said particles, in situ, on said support into a coherent, three-dimensional lattice which is non-swellable in said liquid under analysis, has interconnected void spaces among particles of said lattice to provide transport of said liquid under analysis, and has a void volume of from about 25 to 80 percent.

2. In a method of making an element for the analysis or transport of an aqueous liquid, said element containing a support bearing a particulate structure, said method comprising:
   (a) forming in a liquid carrier a stable dispersion of
      (i) a plurality of heat-stable, organo-polymeric particles non-swellable in and impermeable to said liquid under analysis, said particles having a particle size of from about 1 to 200 microns, and
      (ii) an adhesive latex, in an amount less than 10 percent by weight of said particles, comprising an organic polymer, said adhesive polymer being different from that of said particles, being insoluble in said liquid under analysis, and having a glass transition temperature less than that of said particles; and
   (b) applying said dispersion to said support and removing said liquid carrier at a temperature above the glass transition temperature of said adhesive polymer but below the heat-stability temperature of said particles to concentrate said adhesive at contiguous surface areas of adjacent particles and bond said particles, in situ, on said support into a coherent, three-dimensional lattice which is non-swellable in said liquid under analysis, has interconnected void spaces among particles of said lattice to provide transport of said liquid under analysis, and has a void volume of from about 25 to 80 percent.

3. A method of making an element as defined in claim 2 wherein a surfactant is added to said liquid carrier during step (a) to facilitate formation of said stable dispersion.

4. A method of making an element as defined in claim 2 wherein formation of said stable dispersion in step (a) is facilitated by matching the specific gravity of said heat-stable particles to that of said liquid carrier.

5. A method of making an element as defined in claim 2 wherein formation of said stable dispersion in step (a) is facilitated by matching the specific gravity of said heat-stable particles and that of said liquid carrier to a value within the range of from about 0.7 to 1.3.

6. A method of making an element as defined in claim 2 wherein formation of said stable dispersion in step (a) comprises:

preparing said adhesive as a latex, said latex comprising said adhesive polymer dispersed as a finely-divided discontinuous phase in an aqueous liquid vehicle as a continuous phase; and admixing said heat-stable particles with said latex, said aqueous liquid vehicle of said latex serving as at least a portion of the liquid carrier for said stable dispersion.

* * * * *